United States Patent
Hajjar et al.

(10) Patent No.: US 9,114,148 B2
(45) Date of Patent: Aug. 25, 2015

(54) MODULATING PHOSPHATASE ACTIVITY IN CARDIAC CELLS

(75) Inventors: Roger J. Hajjar, New York, NY (US); Federica del Monte, Boston, MA (US); Evangelia Kranias, Cincinnati, OH (US)

(73) Assignees: University of Cincinnati, Cincinnati, OH (US); The General Hospital Corporation, Boston, MA (US)

( * ) Notice: Subject to any disclaimer, the term of this patent is extended or adjusted under 35 U.S.C. 154(b) by 234 days.

(21) Appl. No.: 11/662,439

(22) PCT Filed: Sep. 8, 2005

(86) PCT No.: PCT/US2005/032162
§ 371 (c)(1),
(2), (4) Date: Sep. 26, 2007

(87) PCT Pub. No.: WO2006/029319
PCT Pub. Date: Mar. 16, 2006

(65) Prior Publication Data
US 2008/0125385 A1    May 29, 2008

Related U.S. Application Data

(60) Provisional application No. 60/608,214, filed on Sep. 9, 2004.

(51) Int. Cl.
| | |
|---|---|
| *A61K 48/00* | (2006.01) |
| *A61K 31/66* | (2006.01) |
| *A01K 67/027* | (2006.01) |
| *C07K 14/47* | (2006.01) |

(52) U.S. Cl.
CPC .......... *A61K 31/66* (2013.01); *A01K 67/0275* (2013.01); *C07K 14/4703* (2013.01); *A01K 2217/052* (2013.01); *A01K 2227/105* (2013.01); *A01K 2267/0375* (2013.01); *A61K 48/00* (2013.01); *C12N 2799/025* (2013.01)

(58) Field of Classification Search
CPC .................. A01K 67/0275; A01K 2217/075; A01K 2217/052; A61K 38/00; A61K 31/66; A61K 48/00; C07K 14/4702; C07K 14/4703; C12N 2799/022; C12N 2830/008; C12N 9/12; C12N 9/1205; C12N 2799/025; C12Q 1/6883
USPC ...................................... 514/44 R; 435/320.1
See application file for complete search history.

(56) References Cited

U.S. PATENT DOCUMENTS

| | | | |
|---|---|---|---|
| 2002/0159978 A1* | 10/2002 | Allen ........................... | 424/93.2 |
| 2004/0214760 A1* | 10/2004 | Gupta et al. .................... | 514/12 |
| 2005/0158281 A1* | 7/2005 | Chamberlain et al. ....... | 424/93.2 |

FOREIGN PATENT DOCUMENTS

| | | |
|---|---|---|
| WO | 02/056837 A2 | 7/2002 |
| WO | WO/2007/100465 | 9/2007 |

OTHER PUBLICATIONS

Kaiser Science, 2007, 317, 580.*
Schroder et al Expert Opin Biol Ther. Sep. 2004;4(9):1413-22.*
Ecke, Goodman & Gilman's The Pharmacological basis of Therapeutics, 1996, McGraw-Hill, New York, NY. pp. 77-101.*
Verma et al Annu Rev Biochem. 2005;74:711-38.*
Hajjar et al Proc. Natl. Acad. Sci., USA, 95, 5251-5256, 1998.*
Thomas et al. Nature Rev.Genet. 4: 346-358; 2003.*
Brockstedt et al Clinical Immunol. 92:67-75; 1999.*
Hajjar et al Circ. Res., Mar. 31, 2000; 86(6): 616-621.*
McTiernan et al Gene Therapy, 2007, 14, 1613-1622.*
Donahue et al, Proc. Natl Aced Sci US A. 1997;94: 4664-4668.*
Sobie et al J Clin Invest. Mar. 2003;111(6):801-3.*
Hoshijima Pharmacology & Therapeutics 105 (2005) 211-228.*
Holschneider et al. Int J Devl Neuroscience, 2000, 18: 615-618.*
Pathak et al Circ Res. 2005;96:756-766.*
Skolnick et al Trends in Biotech, 2000,18, 34-39.*
Pathak et al Circulation, (Oct. 28, 2003) vol. 108, No. 17 Supplement, pp. IV-124.*
Windt et al Proc. Natl Acad Sci., 2001, 98 (6) 3322-3327.*
Bowie, et al. Science, 247: 1306-10, 1990.*
Boekstegers et al Gene Therapy, 2000, 7, 232-240.*
Ponder et al Current Opinion Hematol, 2006, 13, 301-307.*
Emani et al Mol Ther. Aug. 2003;8(2):306-13, abstract.*
Church et al Journal of Veterinary Cardiology, 2007, 9, 53-57.*
Kertesz et al Tex Heart Inst J 1997, 24, 301-307.*
Endo et al Biochemistry, 1996, 35, 5220-5228.*
Xiao et al Journal of Virology, 1999, 3994-4003.*
Carr et al Mol Cell Biol. 2002; 22(12):4124-35.*
Nicolaou et al Circ Res. 2009;104:1012-1020.*
Wittkopper et al the Journal of Clinical Investigation, Feb. 2010, vol. 120, No. 2, 617-626.*
International Search Report and Written Opinion of the International Searching Authority.
Hajjar et al. "Modulation of Ventricular function through gene transfer in vitro." PNAS 95: 5251-5256 (1998).
Ronen Beeri, MD, et al.; *New Efficient Catheter-Based System for Myocardial Gene Delivery*; Circulation; 2002; vol. 106; pp. 1756-1759.
Federica del Monte, MD, PhD, et al.; *Improvement in Survival and Cardiac Metabolism After Gene Transfer of Sarcoplasmic Reticulum $Ca^{2+}$-ATPase in a Rat Model of Heart Failure*; Circulation; 2001; vol. 104; pp. 1424-1429.
Ulrich Gergs et al.; *Overexpression of the Catalytic Subunit of Protein Phosphatase 2A Impairs Cardiac Function*; The Journal of Biological Chemistry; vol. 179; No. 38; Issue of Sep. 24, 2004; pp. 40827-40834.
Yoichi Suzuki, et al; *Insulin Control of Glycogen Metabolism in Knockout Mice Lacking the Muscle-Specific Protein Phosphatase $PP1G/R_{gl}$*; Molecular and Cellular Biology; Apr. 2001; vol. 21; No. 8; pp. 2683-2694.
Neil Brewis, et al; *Dilated cardiomyopathy in transgenic mice expressing a mutant A subunit of protein phosphatase 2A*; American J. Physicol Heart Circ Physiol; vol. 279; pp. H13017-H2000.

(Continued)

*Primary Examiner* — Anoop Singh
(74) *Attorney, Agent, or Firm* — Locke Lord LLP; Jeffrey D. Hsi; Gabriel J. McCool

(57) ABSTRACT

Expression of a phosphatase inhibitor in heart cells can be used to treat cardiac disorders, e.g., heart failure. Decreasing phosphatase activity can improve β-adrenergic responsiveness.

16 Claims, 12 Drawing Sheets

(56) References Cited

OTHER PUBLICATIONS

Federica del Monte, MD, PhD et al.; *Restoration of Contractile Function in Isolated Cardiomyocytes From Failing Human Hearts* by Gene Transfer of SERCA2a.
Peter Boknik, et al.; *Protein phosphatase activity is increased in a rat model of long-term β-αδrenergic stimulation*; Naunyn-Schmiedebertg's Arch Pharmacol; 2000; vol. 362; pp. 222-231.
Michael R. Bristow, M.D., Ph.D., et al.; *Decreased Catecholamine Sensitivity and β-Adrenergic-receptor Density in Failing Human Hearts*; The New England Journal of Medicine; Jul. 22, 1982; vol. 307; No. 4; pp. 205-211.
Philip Cohen; *The Structure and Regulation of Protein Phosphatases*; Advances in Second Messenger and Phosphoproten Research; vol. 24; p. 230-235.
Jeffrey D. Molkentin et al.; *A Calcineurin-Dependent Transcriptional Pathway for Cardiac Hypertrophy*; Cell; vol. 93; Apr. 17, 1998; pp. 215-228.
Boyu Huang, et al.; *Diminished Basal Phosphorylation Level of Phospholamban in the Postinfarction Remodeled Rat Ventricle Role of β-Adrenergic Pathway, $G_i$ Protein, Phosphodiesterase, and Phosphatases*; Circulation Research; vol. 85; No. 9; Oct. 29, 1999; pp. 848-855.
Jern B. Sande, et al.; *Reduced level of serine[16] phosphotylated phospholamban in the failing rat myocardium: a major contributor to reduced DERCA2 activity*; Cardiovascular research; vol. 53; No. 1; Jan. 2002; pp. 382-391.
R. C. Gupta, et al.; *Suplement to Circulation*; vol. 96; No. 8; Oct. 21, 1997; pp. I-361-I362.
Joachim Neumann et al.; *Increased Expression of Cardiac Phosphatases in Patients with End-stage Heart Failure*; J. Mol. Cell Cardiol; vol. 29; Jan. 1997; pp. 265-272.
Helen Kiriazis et al.; *Hypertrophy and functional alterations in hyperdynamic phospholamban-knockout mouse hearts under chronic aortic stenosis*; Cardiovascular Research; vol. 52; 2002; pp. 372-381.
Donald M. Bers; *Cardiac excitation-contrction coupling*; Nature; vol. 415; Jan. 10, 2002; pp. 198-205.
Andrew N. Carr et al.; *Type 1 Phosphatase, a Negative Regulator of Cardiac Function*; Molecular and Cellular Biology; Jun. 2002; vol. 22; No. 12; pp. 4124-4135.
Shogo Endo, et al.; *Multiple Structural elements Define the Specificity of Recombinant Human Inhibitor-1 as a Protein Phosphatase-1 Inhibitor*; Biochemistry; 1996; vol. 35; pp. 5220-5228.
F. Del Monte et al., "Topical Review—Targeting Calcium Cycling Proteins in Heart Failure Through Gene Transfer", Journal of Physiology, 2003, 546-1, pp. 49-61.
Form 1507A, EP, Jun. 4, 2010, Supplemental Europena Search Report for 05804009.
Nicolaou P et al: "Role of protein phosphatase-1 inhibitor-1 in cardiac physiology and pathophysiology" Journal of Molecular and Cellular Cardiology, Academic Press, GB, vol. 47, No. 3, Sep. 1, 2009, pp. 365-371.
Pathak Anand et al: "Enhancement of cardiac function and suppression of heart failure progression by inhibition of protein phosphatase 1." Circulation Research Apr. 15, 2005, pp. 756-766.
Pathak Anand et al: "Therapeutic targeting of the type 1 phosphatase activity in murine models of cardiomyopathy" Circulation, Lippincott Williams & Wilkins, US, vol. 110, No. 17, suppl, Oct. 1, 2004, p. 22.

Carr Andrew N et al: "Type 1 phosphatase, a negative regulator of cardiac function." Molecular and Cellular Biology Jun. 2002 LNKD—PUBMED: 12024026, vol. 22, No. 12, Jun. 2002, pp. 4124-4135.
Pathak Anand et al: "Targeted inhibition of protein phosphatase 1 via expresion of the constitutively active inhibitor-1 protein: A novel molecular inotrope" Circulation, Lipppincott Williams & Wilkims, US, vol. 108, No. 17, suppl, Oct. 28, 2003, pp. IV-124.
Nicolaou Persoulla et al: "Inducible expression of active protein phosphatase-1 inhibitor-1 enhances basal cardiac function and protects against ischemia/reperfusion injury." Circulation Research Apr. 24, 2009 LNKD—PUBMED: 19299645, vol. 104, No. 8, Apr. 24, 2009, pp. 1012-1020.
WO07/100465—Interntaional Search Report (PCT/ISA/210) and Written Opinion of the International Searching Authority (PCT/ISA/237), Kranias et al., University of Cincinnati.
Wittköpper et al., "Constitutively active phosphatase inhibitor-1 improves cardiac contractility in young mice but is deleterious after catecholaminergic stress and with aging," The Journal of Clinical Investigation, Feb. 2010, vol. 120, No. 2, 617-626.
Connor et al., "Cellular Mechanisms Regulating Protein Phosphatase-1," The Journal of Biological Chemistry, Jun. 23, 2000, vol. 275, No. 25, pp. 18670-18675.
Chen et al., "Expression of active protein phosphatase 1 inhibitor-1 attenuates chronic beta-agonist-induced cardiac apoptosis", Basic Res. Cardiol (2010), 105:573-581.
Rodriguez et al., "Identification of a novel phosphorylation site in protein phosphatase inhibitor-1 as a negative regulator of cardiac function", J. Biol. Chem., Dec. 15, 2006; 281(50): 38599-608 Epub. Oct. 17, 2006—cited in IDS from U.S. Appl. No. 12/162,499 companion case.
Bibb, J.A., et al., "Phosphorylation of Protein Phosphatase Inhibitior-1 by Cdk4", The Journal of biological Chemistry, 278(17): 14490-14497 (Apr. 27, 2001).
Braz, J.C., et al., "Pkc-α Regulaes Cardiac Contractility and Propensity Toward Heart Failure", Nature Medicine 10(3): 248-254 (Mar. 2004).
Huang, K. "Ser[67]-Phosphorylated Inhibitor 1 is a Potent ProteinPhosphatase 1 Inhibitor", PNAS 97 (11): 5824-5829 (May 23, 2000).
Rodgriquez, P., et al., Phosphorylation of Human Inhibitor-1 at Ser[67] and/or Thr[75] Attenuates Stimulatory Effects of Protein Kinase A. Signaling inCardiac Myocytes:, Am. J. Physiol. Heart Circ. Physiol. 293: H762-H769 (2007).
Nicolaou et al., "Inducible expression of active protein phosphatase-1 inhibitor-1 enhances basal cardiac function and protects against ischemia/reperfusion injury," Circulation Research, 2009, 104: 1012-1020.
M.R. Snaith et al., "The Use of Transgenic Systems in Pharmaceutical Research," Briefings in Functional Genomics and Proteomics, vol. 1, No. 2, 119-130, Jul. 2002.
Nguyen et al., "The Expanding Role of Mouse Genetics for Understanding Human Biology and Disease," Disease Models & Mechanisms, vol. 56-66, 2008.
Dorn et al., "Manipulating Cardiac Contractility in Heart Failure: Data From Mice and Men," Circulation, 2004, 109: 150-158.

* cited by examiner

A)

B)

C)

```
   1 agtgtcccg gagccgcgag ctggagcgc tgtgccgga gccggagcc gagccgccg
  61 ggctggggcc gggccggag cggagcggag cgggccccag cccgcccag cccgagtcc
 121 cgccgcctc cctcccgccg cagcgcgggc ccaaccagc gtcccgctgc cgcccccagc catggagcaa
 181 gacaacagcc cccaaagat ccagttcacg gaggcgccg ccaccctg tgagccgca ccttgacccc
 241 gaggcggcgg agcagattcg gaggcgcgag agatgaagac cccagcccctg acccacatct gctgaccagt
 301 gaccagtcat cccagagat agatgaagac cggatcccca acccacatct caagtccact
 361 ttgcaatgt ctccacggca acggaagaag atgacaagga tcacacccac aatgaaagag
 421 ctccagatga tggttgaaca tcacctgggg caacagcagc aaggagagga acctgagggg
 481 gccgctgaga gcacaggaac ccaggagtcc cgccacctg ggatcccaga cacagaagtg
 541 gagtcaaggc tgggcacctc tgggacagca aaaaaaactg cagaatgcat ccctaaaact
 601 cacgaaaaag gcagtaagga acccagcaca aagaaccct caacccatat accaccactg
 661 gattccaagg gagccaactc ggtctgaagg aggaggaggt atcttgggat caagactgca
 721 gtttgggaat gcatgacac cggatttgtt tcttattcct tcactttgg ggaaaatctc
 781 ttgtttttaa aaagtgataa atttggtgtt agtccttgg cactttcctt cttttccaac
 841 tgggagaatc ctttctccct gccttcttgc cctgcccctct ctgtagcccc cacctctg
 901 ccaagctgcc tctggaagg aagaaacagg agctaggcag aagccttgag caggaagag
 961 ttcttccctt agcctgact ttacttgctg tggaagaga gatgaggtc agataggtgg
1021 gaggactaac ttccagggtg ccaagaagga agaaagccc caggttctct tttcttattg
1081 aggaacgatc cgacccactc acaggcctgc cctgcagctg gaagactcgg cgctctaagg
1141 cctgtgccgt gtccagctgt gactgctgcgg tgggctccat ctgctggaca aaagggaac
1201 tgcaccatgg cacttgcccc atgggaaaga gggtgtggtg gtgtgccaat acctcctgc
1261 ctgccctcca agcccccagct gccttccttt tggattccca agcttcagga tgtgttcct
1321 cttccagctg tggggaccgct gtccctatt tcaaccgtt agcaacaatg gatagagaac
1381 acagtggcta ttaatgaaga gcccatgct ggagactgga agggttccct tgtcctagac
1441 attgagggc ccagataaga ccaaaaccaa gcataagaga agaaactgtc tcagatctca
1501 cggccaggcc tctctcctgc tgctgttttt gatttttccca ggtagtggga gagaggaaag
1561 gagggaaggc aagattcttt ccccctccct gctgaagcat gtggtacaga ggcaagagca
1621 gagcctgaga agcgtcaggt cgtcagcttg cctgcagct actatgagcc ctcgggcct
1681 cctcctgggc ctcagcttgc ccagatacat ccatgagct acctaaatat atatatatat atatgaggga
1741 gaacgcctca cccagatttt atcatgctgg aaagagtgta tgtatgttgaa gatgcttggt
1801 caacttgtac ccagtgaaca cacaaaaaaa aaaaaaaaa
```

Figure 11A

```
  1 meqdnspqki qftvplleph ldpeaaeqir rrrptpatlv ltsdqsspei dedripnphl
 61 kstlamsprq rkkmtritpt mkelqmmveh hlgqqqgee pegaaestgt qesrppgipd
121 tevesrlgts gtakktaeci pkthergske pstkepsthi ppldskgans v
```

Figure 11B

SEQUENCE LISTING

<160> NUMBER OF SEQ ID NOS: 2

<210> SEQ ID NO 1
<211> LENGTH: 1849
<212> TYPE: DNA
<213> ORGANISM: Homo sapiens

<400> SEQUENCE: 1

```
agagtccccg gagccgcgag ctgggagcgc tgtgccggga gccgggagcc gagcgcgccg      60
ggctggggcc ggggccggag cggagcggag agggagcgcg cccgccccag ccccgagtcc     120
cgccgccttc cctcccgccg cagcgcgggc ccaccggccg ccgcccagc catggagcaa     180 gacaacagcc cccgaaagat ccagttcacg gtcccgctgc tggagccgca ccttgacccc     240
gaggcggcgg agcagattcg gaggcgccgc cccacccctg ccaccctcgt gctgaccagt     300
gaccagtcat ccccagagat agatgaagac cggatcccca acccacatct caagtccact     360
ttggcaatgt ctccacggca acggaagaag atgacaagga tcacacccac aatgaaagag     420
ctccagatga tggtttgaaca tcacctgggg caacagcagc aaggagagga acctgagggg     480
gccgctgaga gcacaggaac ccaggagtcc cgcccacctg ggatcccaga cacagaagtg     540
gagtcaaggc tgggcacctc tgggacagca aaaaaaactg cagaatgcat ccctaaaact     600
cacgagagag gcagtaagga acccagcaca aaagaaccct caacccatat accaccactg     660
gattccaagg gagccaactc ggtctgagag aggaggaggt atcttgggat caagactgca     720
gtttgggaat gcatggacac cggatttgtt tcttattcct tcacttttgg ggaaaatctc     780
```

```
ttgtttttaa aaagtgataa atttggtgtt aggtccttgg cacttctcctt cttttccaac    840
tgggagaatc ctttctccct gccttcttgc cctgccctct ctgtagcccc caccctcctg    900
ccaagctgcc tctgggaagg aagaaacagg agctaggcag aagccttgag cagggaagag    960
ttcttccctt agccctgact ttacttgctg tgggaagaga gatgagggtc agataggtgg   1020
gaggactaac ttccagggtg ccaagaagga agaaaagccc caggttctct tttcttattg   1080
aggaacgatc cgaccacctc acaggcctgc cctgcagctg gaagactcgg cgctctaagg   1140
cctgtgccgt gtccagctgt gactgtgcgg tgggctccat ctgctggaca aaggggaac    1200
tgcaccatgg cacttggccc atgggaaaga gggtatggtg gtgtgccgat acctcctcgc   1260
ctgcccctcca agccccagct gccttccttt tggattccca agcttcagga tgtgttccct   1320
cttccagctg tgggaccgct gtcccttatt tcaacccgtt agcaacaatg atagagaac    1380
acagtggcta ttaatgaaga ggcccatgct ggagactgga agggttccct tgtcctagac   1440
attgaggggc ccagataaga ccaaaaccaa gcataagaga agaaactgtc tcagatctca   1500
cggccaggcc tctctcctgc tgctgttttt gattttccca ggtagtggga gagaggaaag   1560
gagggaaggc aagattctttt ccccctccct gctgaagcat gtggtacaga ggcaagagca   1620
gagcctgaga agcgtcaggt cccacttctg ccatgcagct actatgagcc ctcgggcct    1680
cctcctgggc ctcagcttgc ccagatacat acctaaatat atatatatatat atatatgagg  1740
gagaacgcct cacccagatt ttatcatgct ggaaagagtg tatgtatgtg aagatgcttg   1800
gtcaacttgt acccagtgaa cacacacagt caggaaaaaa aaaaaaaa              1849
```

<210> SEQ ID NO 2
<211> LENGTH: 171
<212> TYPE: PRT
<213> ORGANISM: Homo sapiens

<400> SEQUENCE: 2

Met Glu Gln Asp Asn Ser Pro Arg Lys Ile Gln Phe Thr Val Pro Leu
1               5                   10                  15

Leu Glu Pro His Leu Asp Pro Glu Ala Ala Glu Gln Ile Arg Arg Arg
            20                  25                  30

Arg Pro Thr Pro Ala Thr Leu Val Leu Thr Ser Asp Gln Ser Ser Pro
        35                  40                  45

Glu Ile Asp Glu Asp Arg Ile Pro Asn Pro His Leu Lys Ser Thr Leu
    50                  55                  60

Ala Met Ser Pro Arg Gln Arg Lys Lys Met Thr Arg Ile Thr Pro Thr
65                  70                  75                  80

Met Lys Glu Leu Gln Met Met Val Glu His His Leu Gly Gln Gln Gln
                85                  90                  95

Gln Gly Glu Glu Pro Glu Gly Ala Ala Glu Ser Thr Gly Thr Gln Glu
            100                 105                 110

Ser Arg Pro Pro Gly Ile Pro Asp Thr Glu Val Glu Ser Arg Leu Gly
        115                 120                 125

Thr Ser Gly Thr Ala Lys Lys Thr Ala Glu Cys Ile Pro Lys Thr His
    130                 135                 140

Glu Arg Gly Ser Lys Glu Pro Ser Thr Lys Glu Pro Ser Thr His Ile
145                 150                 155                 160

Pro Pro Leu Asp Ser Lys Gly Ala Asn Ser Val
                165                 170

MODULATING PHOSPHATASE ACTIVITY IN CARDIAC CELLS

RELATED APPLICATIONS/PATENTS & INCORPORATION BY REFERENCE

This application is the U.S. national phase application, pursuant to 35 U.S.C. §371, of International Patent Application No. PCT/US2005/032162, filed Sep. 8, 2005, designating the United States, and published in English on Mar. 16, 2006 as International Publication No. WO 2006/029319 A2, which claims priority to U.S. Application Ser. No. 60/608,214 filed on Sep. 9, 2004, the contents of all of which are hereby expressly incorporated herein by reference.

STATEMENT OF GOVERNMENT INTEREST

The United States government has certain rights in this invention by virtue of grant numbers HL64018, HL52318, HL 57623, HL26057, DK36569 and HL07382-27 from the National Institutes of Health.

SEQUENCE LISTING

This application contains a Sequence Listing which has been submitted in ASCII format via EFS-Web and is hereby incorporated by reference in its entirety. Said ASCII copy, created on Oct. 13, 2010, is named 63653588.txt and is 4,333 bytes in size.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

BACKGROUND

Reversible protein phosphorylation represents the cellular basis for integration of key signaling pathways, mediating a fine crosstalk between external effector molecules and intracellular events. In the heart, Ca2+ cycling and contractility are controlled by a fine balance of protein kinase and phosphatase activities, in response to various second messenger signals.

Demands on the heart's pumping action, during fight-or-flight situations, can increase human cardiac output by nearly 5-fold, and this is linked to β-adrenergic activation of the camp dependent protein kinase (PKA). PKA then phosphorylates a set of key regulatory Ca2+ handling proteins that control excitation-contraction coupling cycle, such as phospholamban, the ryanodine receptor, the L-type channel Ca2+ and troponin I (Bers, D. M., 2002 *Nature;* 415:198-205).

Although the protein kinases and their phospho-protein substrates, underlying augmentation of the heart's pumping action have been well characterized, similar studies on the protein phosphatases, reversing the increased cardiac contractility are less well developed. Stemming from a common gene family, the major Ser/Thr phosphatases (type 1, type 2A and type 2B (calcineurin), are highly homologous proteins (40-50%) (Cohen, P., 1990 Phosphoprotein Res; 24:230-5) that play critical roles in the control of cardiac contractility and hypertrophy. Overexpression of the catalytic subunit of protein phosphatase 2A has been shown to decrease cardiac function and lead to a pathologic cardiac hypertrophy (Brewis, N. et al., 2000 *Am J Physiol Heart Circ Physiol;* 279:H1307-18; Gergs, U. et al., 2004 *J Biol Chem.*). Furthermore, calcineurin, a calcium dependent phosphatase, induces hypertrophy by its regulation of the NFAT transcription factor activity. 5 Interestingly, inhibition of this phosphatase blocks cardiac hypertrophy in vivo and in vitro (Brewis, N. et al., 2000; Molkentin, J. D., 1998 *Cell;* 93:215-28).

In human and experimental heart failure, the activity of the type 1 phosphatase associated with the sarcoplasmic reticulum (SR) is significantly increased, suggesting that this may be a contributing factor to depressed function, dilated cardiomyopathy and premature death (Huang, B. et al., 1999 *Circ Res;* 85:848-55; Sande, J. B., et al., 2002 *Cardiovasc Res;* 53:382-91; Boknik, P. et al., 2000 *Naunyn Schmiedebergs Arch Pharmacol;* 362:222-31; Gupta, R. C. et al., 1997 *Circulation;* 96 (Suppl 1): I-361; Neumann, J. 1997 *J Mol Cell Cardiol;* 29:265-72; Carr, A. N. et al., 2002, *Mol Cell Biol;* 22:4124-35). However, the role of phosphatase inhibition in β-adrenergic responsiveness was not previously known.

SUMMARY OF THE INVENTION

It has now been discovered, inter alia, that expression of a phosphatase inhibitor in heart cells can be used to treat cardiac disorders, e.g., heart failure. Decreasing phosphatase activity can improve β-adrenergic responsiveness.

Accordingly, in one aspect, this disclosure features a method that includes administering, into heart cells, e.g., cardiomyocytes, an agent that modulates phosphatase activity, e.g., type 1 phosphatase activity, in the cells. The heart cells can be in vitro or in vivo. For example, the heart cells can be in a heart of a subject. The method can be used to treat a subject, e.g., a subject having a cardiac disorder, e.g., heart failure. Typically, the subject is a mammal, e.g., a human or non-human mammal.

Type 1 phosphatases include, but are not limited to, PP1cα, PP1cβ, PP1cδ and PP1cγ.

In one embodiment, the agent is a nucleic acid that comprises a sequence encoding a protein that inhibits phosphatase activity, e.g., type 1 phosphatase activity. The agent can be administered in an amount effective to decrease phosphatase activity and/or increase β-adrenergic responsiveness in the treated cells.

In another embodiment, the agent is a nucleic acid that increases expression of an endogenous nucleic acid that encodes a protein that inhibits phosphatase activity. For example, the nucleic acid can include a sequence that encodes a transcription factor, e.g., an engineered transcription factor such as a chimeric zinc finger protein. In still another example, the nucleic acid is a regulatory sequence that integrates in or near the endogenous nucleic acid that encodes a protein that inhibits phosphatase activity, e.g., in or near a gene encoding phosphatase inhibitor-1 ("I-1").

In still another embodiment, the agent is a nucleic acid that can provide a nucleic acid modulator of gene expression. For example, the nucleic acid can be a nucleic acid that can express such a nucleic acid modulator, e.g., a dsRNA (e.g., siRNA), an anti-sense RNA, or a ribozyme.

The agent can be delivered using a viral particle, e.g., a virus or a virus-like particle. The viral particle can be derived from an adeno-associated virus, an adenovirus, or a lentivirus.

In one embodiment, the viral particle is introduced by an injection, e.g., a direct injection into the heart, e.g., a direct injection into the left ventricle surface. In another embodiment, the viral particle is introduced into a lumen of the circulatory system, e.g., into a chamber or the lumen of the heart or a blood vessel of the heart of a subject. For example, the pericardium can be opened and the compound can be injected into the heart, e.g., using a syringe and a catheter. The compound can be introduced into the lumen of the aorta, e.g., the aortic root, introduced into the coronary ostia or introduced into the lumen of the heart. The viral particle can be introduced into a coronary artery. It is also possible to restrict blood flow to increase resident time in the blood vessel, e.g., in the coronary artery, e.g., using an antegrade or retrograde blockade.

In one embodiment, the viral particle is introduced by a percutaneous injection, e.g., retrograde from the femoral artery retrograde to the coronary arteries. In still another embodiment, the viral particle is introduced, e.g., using a stent. For example, the viral particle is coated on the stent and the stent is inserted into a blood vessel, such as a coronary artery, peripheral blood vessel, or cerebral artery.

In one embodiment, introducing the viral particle includes restricting blood flow through coronary vessels, e.g., partially or completely, introducing the viral delivery system into the lumen of the coronary artery, and allowing the heart to pump, while the coronary vein outflow of blood is restricted. Restricting blood flow through coronary vessels can be performed, e.g., by inflation of at least one, two, or three angioplasty balloons. Restricting blood flow through coronary vessels can last, e.g., for at least one, two, three, or four minutes. Introduction of the viral particle into the coronary artery can be performed, e.g., by an antegrade injection through the lumen of an angioplasty balloon. The restricted coronary vessels can be: the left anterior descending artery (LAD), the distal circumflex artery (LCX), the great coronary vein (GCV), the middle cardiac vein (MCV), or the anterior interventricular vein (AIV). Introduction of the viral particle can be performed after ischemic preconditioning of the coronary vessels, e.g., by restricting blood flow by e.g., inflating at least one, two, or three angioplasty balloons. Ischemic preconditioning of the coronary vessels can last for at least one, two, three, or four minutes.

In one embodiment, introducing the viral particle includes restricting the aortic flow of blood out of the heart, e.g., partially or completely, introducing the viral delivery system into the lumen of the circulatory system, and allowing the heart to pump, e.g., against a closed system (isovolumically), while the aortic outflow of blood is restricted. Restricting the aortic flow of blood out of the heart can be performed by redirecting blood flow to the coronary arteries, e.g., to the pulmonary artery. Restricting the aortic flow of blood can be accomplished by clamping, e.g., clamping a pulmonary artery. Introducing the viral particle can be performed e.g., with the use of a catheter or e.g., by direct injection. Introducing the viral particle can be performed by a delivery into the aortic root.

In one embodiment, the number of viral particles that are administered are e.g., at least $1\times10^9$, $1\times10^{10}$, $1\times10^{11}$, $1\times10^{12}$, $1\times10^{13}$, $1\times10^{14}$, $1\times10^{15}$, or $1\times10^{16}$ units (e.g., genomes or plaque forming units), or, for example, between $1\times10^9$ to $1\times10^{18}$ or $1\times10^{11}$ to $1\times10^{16}$.

The agent can also be delivered using means other than a viral particle, e.g., a liposome or other non-viral delivery vehicle.

In another aspect, the disclosure features a viral particle that can enter cells. The particle includes a nucleic acid encoding a non-viral protein, e.g., a protein that decreases phosphatase activity or a protein that modulates cardiac activity. The viral particle can be a virus or virus-like particle. In one embodiment, the viral particle is derived from an adeno-associated virus. The adeno-associated virus can be of serotype 1 (AAV1), serotype 2 (AAV2), serotype 3 (AAV3), serotype 4 (AAV4), serotype 5 (AAV5), serotype 6 (AAV6), serotype 7 (AAV7), serotype 8 (AAV8), or serotype 9 (AAV9). For example, the viral particle is a modified adeno-associated virus or a reconstituted virus or virus-like particle, e.g., that can infect cells, e.g., a myocytes, e.g., a cardiomyocyte.

In another embodiment, the viral particle is derived from a lentivirus or an adenovirus.

Examples of proteins that modulate cardiac activity include: a protein that modulates phosphatase activity (e.g., a phosphatase type 1 inhibitor, e.g., I-1) or a sacroplasmic reticulum $Ca^{2+}$ ATPase (SERCA), e.g., SERCA1 (e.g., 1a or 1b), SERCA2 (e.g., 2a or 2b), or SERCA3.

The disclosure also features a preparation that includes one or more doses of a viral delivery system described herein. A dose can include, e.g., at least $1\times10^9$, $1\times10^{10}$, $1\times10^{11}$, $1\times10^{12}$, $1\times10^{13}$, $1\times10^{14}$, $1\times10^{15}$, or $1\times10^{16}$ units (e.g., genomes or plaque forming units) of the viral delivery system. In one embodiment, at most $1\times10^{19}$ units of the viral delivery system are in a dose. The preparation can be a cell-free preparation, e.g., a pharmaceutical preparation, e.g., one that is suitable for introduction into a subject. The preparation can also contain less than 10, 5, 1, 0.1, or 0.001% pfu of wild-type virus (i.e., virus that can replicate and that does not include a non-viral nucleic acid sequence). In one embodiment, the preparation is free of wild-type virus.

The disclosure also features a stent that includes an agent that decreases phosphatase activity, e.g., in a cardiomyocyte. For example, the agent can be coated on the stent. For example, the agent can be within a viral particle and the viral particle is coated on one or more surfaces of the stent, e.g., a surface that contacts the blood vessel. A "stent" is a medical device configured for implantation in a body lumen to prevent or inhibit the closing of the lumen. A stent can be configured to be implanted in, e.g., a blood vessel such as an artery, or other body cavity, orifice or duct, such as a urethra. A stent is typically made of biocompatible metal or plastic. As used herein, a stent "coated with or containing" an agent means a stent having the agent either affixed to its surface or contained within it, so as to permit release of the agent from the stent and, hence, delivery of the agent to tissue in proximity with the stent.

A subject can be treated by implanting a stent in an afflicted blood vessel of the subject. The blood vessel is, for example, a coronary artery, and can also be, for example, a peripheral artery or a cerebral artery.

The term "treating" refers to administering an agent in amount, manner, and/or mode effective to improve a condition, symptom, or parameter associated with a disorder or to prevent progression of a disorder, to either a statistically significant degree or to a degree detectable to one skilled in the art. An effective amount, manner, or mode can vary depending on the subject and may be tailored to the subject. For example, the mode of administration can include delivery by a virus or virus-like particle. By preventing progression of a disorder, a treatment can prevent deterioration of a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "heart disorder" refers to a structural or functional abnormality of the heart that impairs its normal functioning. For example, the heart disorder can be heart failure, ischemia, myocardial infarction, congestive heart failure, arrhythmia, transplant rejection and the like. The term includes disorders characterized by abnormalities of contraction, abnormalities in $Ca^{2+}$ metabolism, and disorders characterized by arrhythmia.

The term "heart failure" refers to any of a number of disorders in which the heart has a defect in its ability to pump adequately to meet the body's needs. In many cases, heart failure is the result of one or more abnormalities at the cellular level in the various steps of excitation-contraction coupling of the cardiac cells. One such abnormality is a defect in SR function.

As used herein, the term "heart cell" refers to a cell which can be: (a) part of a heart present in a subject, (b) part of a heart which is maintained in vitro, (c) part of a heart tissue, or (d) a cell which is isolated from the heart of a subject. For example, the cell can be a cardiac myocyte.

As used herein, the term "heart" refers to a heart present in a subject or to a heart which is maintained outside a subject.

As used herein, the term "heart tissue" refers to tissue which is derived from the heart of a subject.

As used herein, the term "somatic gene transfer" refers to the transfer of genes into a somatic cell as opposed to transferring genes into the germ line.

As used herein, the term "compound" refers to a compound, which can be delivered effectively to the heart of a subject using the methods of the invention. Such compounds can include, for example, a gene, a drug, an antibiotic, an enzyme, a chemical compound, a mixture of chemical compounds or a biological macromolecule.

As used herein, the term "restricting blood flow" refers to substantially blocking the flow of blood through a vessel, e.g., flow of blood into the distal aorta and its branches. For example, at least 50% of the blood flowing out of the heart is restricted, preferably 75% and more preferably 80, 90, or 100% of the blood is restricted from flowing out of the heart. The blood flow can be restricted by obstructing the aorta and the pulmonary artery, e.g., with clamps.

A "viral delivery system" refers to a viral particle, e.g., virus or virus like particle that can introduce a nucleic acid that includes a non-viral sequence into a mammalian cell. The viral delivery system itself may or may not be competent for viral replication.

These and other objects of the invention will be described in further detail in connection with the detailed description of the invention.

BRIEF DESCRIPTION OF THE DRAWINGS

The following Detailed Description, given by way of example, but not intended to limit the invention to specific embodiments described, may be understood in conjunction with the accompanying drawings, incorporated herein by reference. Various preferred features and embodiments of the present invention will now be described by way of non-limiting example and with reference to the accompanying drawings, in which:

FIG. 6A shows, in bar-graph form, the cross-sectional area of banded WT and I-1* cardiomyocytes. *$P<0.001$ vs. Sham surgery; † $P<0.05$ between WT-banded and I-1* banded hearts; n>120 cardiomyocytes per group.

FIGS. 11A and 11B depict the nucleic acid sequence (SEQ ID NO:1), GenBank accession No. NM_006741, encoding the phosphatase inhibitor-1 ("I-1") protein (SEQ ID NO:2), GenBank accession No. NP_006732.2.

DETAILED DESCRIPTION

Figure 1:
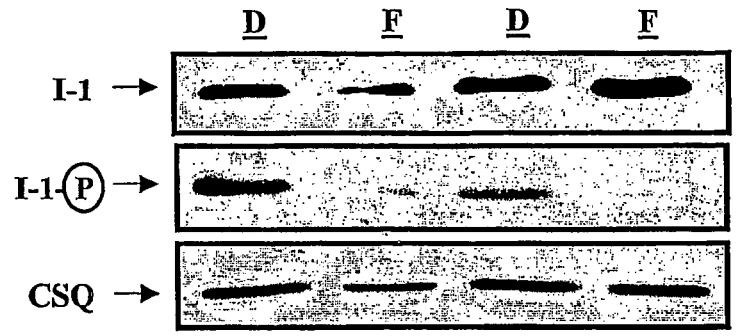
FIGS. 1A and 1B exhibit results indicating that phosphatase inhibitor-1 ("I-1") phosphorylation is significantly decreased in failing human hearts: (A) Representative immunoblots of the protein levels (top) and phosphorylation (middle) of I-1 in 9 nonfailing donor (D) and 10 failing (F) heart homogenates. The calsequestrin levels (CSQ, bottom) were assessed in the same blots and were used as an internal control. (B) Quantitation of I-1 protein levels in human hearts revealed no alterations. However, I-1 phosphorylation was significantly decreased in failing human hearts. * indicates $P<0.05$ vs. nonfailing donor hearts.
Figure 1:
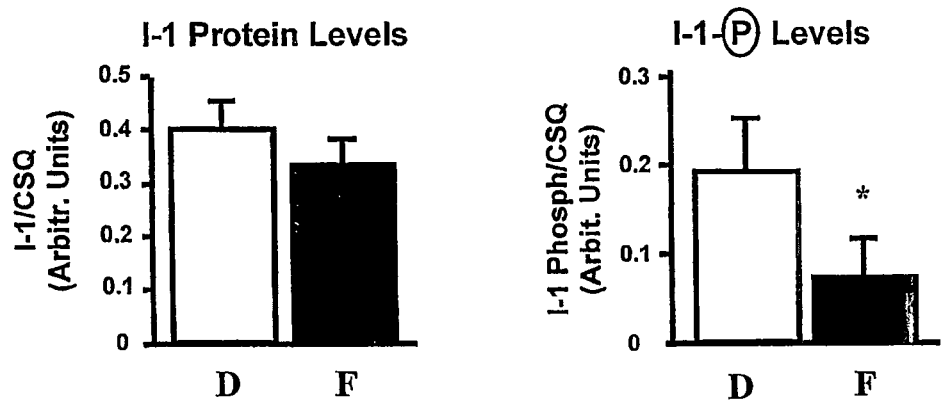

Phosphatase activity is increased in heart failure. Reducing phosphatase activity (e.g., phosphatase 1 activity) in cardiomyocytes can relieve one or more symptoms of associated with heart failure. Reduced phosphatase activity is associated with attenuated β-adrenergic responsiveness.

In one embodiment, phosphatase activity can be decreased by inhibiting type 1 phosphatases. Type 1 phosphatases include, but are not limited to PP1cα, PP1cβ, PP1cδ and PP1cγ. See Sasaki et. al. (1990) Jpn J Cancer Res. 81: 1272-1280, the contents of which are incorporated herein by reference. The phosphatase inhibitor-1 (or "I-1") protein is an endogenous inhibitor of type 1 phosphatase. Increasing I-1 levels or activity can restore β-adrenergic responsiveness in failing human cardiomyocytes.

In specific embodiments, a constitutively active I-1 protein can be administered. One such construct exemplified herein (I-1$_{T35D}$) entails truncation of the I-1 cDNA to encode for the first 65 amino acids and introduction of nucleotide changes to replace the PKA phosphorylation site (ACC:Thr$^{35}$) with aspartic acid (GAC:Asp$^{35}$), resulting in a constitutively active inhibitor. Another way to make a constitutively active inhibitor is to substitute threonine 35 with glutamic acid instead of aspartic acid. These substitutions can also be made in a full length inhibitor molecule. Failing human cardiomyocytes expressing I-1$_{T35D}$ exhibit normal contractile function under basal conditions and their beta adrenergic function is restored to normal. Thus, delivery of inhibitor-1 completely restores function and reverses remodeling in the setting of pre-existing heart failure.

Other phosphatase inhibitors and other variants of I-1 can also be used. Examples of such other inhibitors include phosphatase inhibitor 2; okadaic acid or caliculin; and nipp1 which is an endogenous nuclear inhibitor of protein phosphatase 1. In one embodiment, the phosphatase inhibitor is specific for protein phosphatase 1.

Other methods for decreasing phosphatase activity include administering small molecules that enhance the activity of a phosphatase inhibitor, e.g., I-1, administering small molecules that decrease the activity of type 1 phosphatases, administering nucleic acids that decrease the activity or expression of type 1 phosphatases, or administering nucleic acids that increase the activity or expression of a phosphatase inhibitor.

Phosphatase Activity in Heart Failure:

Cardiac muscle function on a beat-to-beat basis is a highly regulated process through the body's sympathetic tone. In seconds, the heart may respond to increases in workload by increasing cardiac output to support the demands of peripheral, metabolizing tissues. This adaptive mechanism, enhancing the inotropic state of the heart, is controlled in large part by the catecholamine-dependent activation of myocardial β-receptors. These receptors are found on the cardiac cells that enhance the strength of contraction when stimulated or activated. At the cellular level, stimulation of the β-receptors (Koch, W. J. et al., 2000 Annu Rev Physiol; 62: 237-60) results in increases in cAMP levels, activation of the cAMP-dependent protein kinase (PKA) and phosphorylation of enzymes involved in energy metabolism as well as key regulator proteins, recruited to modulate contractility and increase stroke volume. The major regulatory phosphoproteins include phospholamban (PLB), the ryanodine receptor, the L-type Ca$^{2+}$ channel, troponin I, and C-protein.

PLB is the major regulator of basal myocardial contractility and a key mediator of the inotropic and lusitropic effects of β-agonists which bind to the beta receptors and increase the strength of contraction of the cardiac cells in the mammalian heart (Brittsan, A. G. et al., 2003 Circ Res; 92:769-76). Phosphorylation of PLB relieves its inhibition of SERCA, which greatly stimulates the rate and amount of cytosolic calcium re-sequestered into the sacroplasmic reticulum (SR), enhancing myocardial relaxation. This increased calcium cycling profile is associated with enhanced SR calcium content allowing for increased quantal calcium release during subsequent contractions. Collectively, these events result in enhanced systolic and diastolic function.

Increases in protein phosphorylation and enhanced cardiac function are reversed by protein phosphatases in an efficient and highly regulated process. Two main classes of serine/threonine phosphatases, referred to as phosphatase types 1 and 2 regulate cardiac muscle contractile performance (Neumann, J. et al., 1997 J Mol Cell Cardiol; 29 (1): 265-72).

Protein phosphatase 1 ("PP1") accounts for a significant amount of the cardiac enzymatic activity, and has been implicated as the key class of regulatory phosphatase enzymes. PP1 is largely associated with the membrane fraction as well as glycogen particles and is important in glycogenolysis and glycogen synthesis. It is anchored to these locales by large, non-catalytic targeting subunits, which serve to enhance substrate availability and specificity. Furthermore, this enzyme is regulated by two heat and acid stable proteins, inhibitors-1 and -2. Phosphatase Inhibitor-1 ("I-1") is the main physiological modulator and is an effective inhibitor when phosphorylated on threonine-35 by PKA (Endo, S. et al., 1996 Biochemistry; 35 (16): 5220-8). Inhibition of PP1, removes its opposition to the actions of PKA protein phosphorylation, leading to amplification of the β-agonist responses in the heart (Ahmad, Z. J. 1989 Biol Chem; 264:3859-63; Gupta, R. C. et al., 1996 Circulation; (Suppl 1): I-361).

This fine-tuning regulation of cardiac regulatory protein phosphorylation by protein kinases and phosphatases becomes even more important in heart failure, since decreases in cAMP levels by desensitization of β-receptors (Koch, Lefkowitz et al. 2000) would be expected to lead to inactivation of PKA, while the levels and activity of protein phosphatase 1 are increased.

Viral Vectors Suitable for Somatic Gene Transfer

A therapeutic nucleic acid, e.g., a nucleic acid that decreases phosphatase activity or a nucleic acid that provides a nucleic acid modulator of expression (e.g., dsRNA, an antisense RNA, or a ribozyme), e.g., as described herein, can be incorporated into a gene construct to be used as a part of a gene transfer protocol. Approaches include insertion of the subject gene in viral vectors, e.g., recombinant vectors derived from retroviruses (e.g., replication defective retroviruses), adenovirus (e.g., replication deficient, first generation, or gutted, second generation, adenovirus), adeno-associated virus (e.g., any of types 1-6), lentivirus, and herpes simplex virus-1, or recombinant bacterial or eukaryotic plasmids. Viral vectors can also be used to transfect cells directly. Viral particles that delivery a therapeutic nucleic acid can be made from modified viruses. Modified viruses can include an alteration to at least one viral sequence, e.g., replacement, deletion, or inactivation of one or more viral genes.

Exemplary adenoviral vectors include (Ad.RSV.lacZ), which includes the Rous sarcoma virus promoter and the lacZ reporter gene as well as (Ad.CMV.lacZ), which includes the cytomegalovirus promoter and the lacZ reporter gene. See, e.g., U.S. Ser. No. 10/914,829. The lacZ sequence can be replaced with the sequence that encodes the protein or nucleic acid modulator of expression. Methods for the preparation and use of viral vectors are described, e.g., in WO 96/13597, WO 96/33281, WO 97/15679, Miyamoto et al. (2000) Proc Natl Acad Sci USA 97 (2):793-8, and Trapnell et al., Curr. Opin. Biotechnol. 5 (6):617-625, 1994.

Adeno-associated virus is a nonpathogenic human parvovirus, capable of site-specific integration into chromosome 19. Fisher et al., Nature Medicine 3 (3):306-312, 1997. Replication of the virus, however, requires a helper virus, such as an adenovirus. Fisher et al., Nature Medicine 3 (3):306-312, 1997. An AAV coding region can be replaced with nonviral genes, and the modified virus can be used to infect both dividing and non-dividing cells. Xiao et al., J. Virol. 70 (11): 8098-8108, 1996; Kaplitt et al., Ann. Thorac. Surg. 62: 1669-1676, 1996. Exemplary methods for the preparation and use of AAVs are described in Fisher et al., Nature Medicine 3 (3):306-312, 1997; Xiao et al., J. Virol. 70 (11): 8098-8108, 1996; Kaplitt et al., Ann. Thorac. Surg. 62:1669-1676, 1996.

AAV6 is specific and confers fast expression in the heart. For example, U.S. Ser. No. 10/914,829 demonstrates that gene transfer with AAV6 in the heart of a large animal is efficient and can lead to long-lasting gene expression.

Methods for producing modified AAV particles have been developed. For example, cells are grown in culture are caused to produce modified AAV particles. The particles are harvested from the cells and purified. Exemplary production methods for AAV particles involve delivery of three elements to the producer cells: 1) a gene of interest (e.g., a sequence the modulates phosphatase activity) flanked by AAV ITR sequences, 2) AAV rep and cap genes, and 3) helper virus proteins ("helper functions"). The conventional protocol for delivering the first two is by transfection of the cells with plasmid DNA containing the appropriate recombinant gene cassettes. The helper functions have traditionally been supplied by infecting the cells with a helper virus such as adenovirus (Ad). (Samulski et al., 1998; Hauswirth et al., 2000).

Lentiviruses are a subgroup of retroviruses that are capable of infecting non-dividing cells. L. Naldini et al. report a lentiviral vector system based on the human immunodeficiency virus (HIV) that is capable of transducing heterologous gene sequences into non-proliferative HeLa cells and rat fibroblasts, as well as into human primary macrophages and terminally differentiated neurons. Science 272, 263-267 (1996). U.S. Pat. No. 6,521,457 describes a lentiviral vector based on Equine Infectious Anemia Virus. U.S. Pat. No. 6,428,953 describes additional lentiviral vectors and methods for producing lentiviral particles.

To produce a lentiviral particle and other viral particles, the nucleic acid that encodes the agent of interest (e.g., an agent that decreases phosphatase activity) is operably linked to a packaging signal. The nucleic acid is packaged in cells that express viral structural proteins. For example, the cells can include nucleic acids that encode the viral structural proteins, but that lack a packaging signal.

Non-viral methods are also available. For example, plasmid DNA can be delivered, e.g., using cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo.

Gene transfer into cardiovascular tissue has been successful using adenovirus (Ad) vectors with strong, non-tissue specific gene expression cassettes driven by cytomegalovirus (CMV) or Rous sarcoma virus (RSV) promoters. Clinical trials involving transduction of cardiac cells with viral vectors to deliver angiogenic factors such as vascular endothelial cell growth factor (VEGF), fibroblast growth factor (FGF) and hepatocyte growth factor (HGF) have been ongoing. Intra-aorta or intracoronary injection of virus has been used in vivo in animal models. In one study, intracardiac injection of an Ad-SERCA2a viral vector in rats was sufficient to induce physiological improvement in calcium handling. See Miyamoto et al., 2000, Proc. Natl. Acad. Sci. USA 97:793-98. Adenoviral vectors have also been used in vivo to express β2 adrenergic receptor (β-AR) (see Maurice et al. 1999, J. Clin. Invest. 104:21-9 and Shah et al., 2001, Circulation. 103: 1311). As is known from studies on cystic fibrosis, transduction of all cells in a tissue is not required for improved function. For example, expression of the wild type sodium channel in as few as 6-10% of cells within an epithelial sheet lacking a functional sodium channel is sufficient for normal sodium ion transport (Johnson et al, 1992, Nat. Genet 2:21-5). This is known as the bystander effect.

The promoter can be, e.g., a smooth muscle specific promoter, such as a smooth muscle alpha actin promoter, SM22a promoter; cardiac specific promoter, such as a cardiac myosin promoter (e.g., a cardiac myosin light chain 2v promoter), troponin T promoter, or BNP promoter. The promoter can also be, e.g., a viral promoter, such as CMV promoter. Tissue specific promoters have been used to increase specificity of myocardial gene expression (Rothmann et al., 1996, *Gene Ther.* 3:919-26).

The efficiency of cardiomyocyte gene delivery by an adeno-associated virus (AAV) vector was documented in vitro using cultured rat neonatal cells, as well as in an ex vivo system using rat papillary muscle immersion (Maeda et al., 1998, *J. Mol. Cell. Cardiol.* 30:1341-8). Ex vivo AAV vector transfer followed by syngeneic heart transplantation was reported to achieve high efficiency marker gene expression (Svensson et al., 1999, *Circulation.* 99:201-5).

Methods of achieving a high level of in vivo cardiotopic gene transfer with high consistency (average 60-70% of cardiac myocytes) are described, e.g., in US Published Application 2002-0032167. Other methods for the preparation and use of viral vectors are described in WO 96/13597, WO 96/33281, WO 97/15679, and Trapnell et al., 1994, *Curr. Opin. Biotechnol.* 5 (6):617-625; Ardehali et al., 1995, *J. Thorac. Cardiovasc. Surg.* 109:716-720; Dalesandro et al., 1996, *J. Thorac. Cardiovasc. Surg.* 111:416-422; Sawa et al., 1995, Circ 92, II479-11482; Lee et al., 1996, *J. Thorac. Cardiovasc. Surg.* 111, 246-252; Yap et al., 19996, Circ. 94, I-53; and Pellegrini et al., 1998, *Transpl. Int.* 11, 373-377.

A subject polynucleotide can also be administered using a non-viral delivery vehicle. "Non-viral delivery vehicle" (also referred to herein as "non-viral vector") as used herein is meant to include chemical formulations containing naked or condensed polynucleotides (e.g., a formulation of polynucleotides and cationic compounds (e.g., dextran sulfate)), and naked or condensed polynucleotides mixed with an adjuvant such as a viral particle (i.e., the polynucleotide of interest is not contained within the viral particle, but the transforming formulation is composed of both naked polynucleotides and viral particles (e.g., adenovirus particles) (see, e.g., Curiel et al. 1992 *Am. J. Respir. Cell Mol. Biol.* 6:247-52). Thus, a "non-viral delivery vehicle" can include vectors composed of polynucleotides plus viral particles where the viral particles do not contain the polynucleotide of interest. Exemplary "non-viral delivery vehicles" include bacterial plasmids, viral genomes or portions thereof, wherein the polynucleotide to be delivered is not encapsidated or contained within a viral particle, and constructs comprising portions of viral genomes and portions of bacterial plasmids and/or bacteriophages. The term also encompasses natural and synthetic polymers and co-polymers. The term further encompasses lipid-based vehicles.

Lipid-based vehicles include cationic liposomes such as disclosed by Feigner et al (U.S. Pat. Nos. 5,264,618 and 5,459,127; PNAS 84:7413-7417, 1987; *Annals New York Acad. Sci.* 772:126-139, 1995); they may also consist of neutral or negatively charged phospholipids or mixtures thereof including artificial viral envelopes as disclosed by Schreier et al. (U.S. Pat. Nos. 5,252,348 and 5,766,625).

Non-viral delivery vehicles include polymer-based carriers. Polymer-based carriers may include natural and synthetic polymers and co-polymers. For example, the polymers are biodegradable, or can be readily eliminated from the subject. Naturally occurring polymers include polypeptides and polysaccharides. Synthetic polymers include, but are not limited to, polylysines, and polyethyleneimines (PEI; Boussif et al., PNAS 92:7297-7301, 1995) which molecules can also serve as condensing agents. These carriers may be dissolved, dispersed or suspended in a dispersion liquid such as water, ethanol, saline solutions and mixtures thereof. A wide variety of synthetic polymers are known in the art and can be used.

The pharmaceutical preparation of the gene therapy construct can include the gene delivery system and an acceptable diluent, or can include a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system. However, typically the preparation is cell-free. The preparation generally includes materials that do not interrupt ability of viral particles to delivery nucleic acid into cells.

The nucleic acid to be delivered can also be formulated as a DNA- or RNA-liposome complex formulation. Such complexes comprise a mixture of lipids which bind to genetic material (DNA or RNA) by means of cationic charge (electrostatic interaction). Cationic liposomes which may be used in the present invention include 3θ-[N-(N',N'-dimethyl-aminoethane)-carbamoyl]-cholesterol (DC-Chol), 1,2-bis(oleoyloxy-3-trimethylammonio-pr-opane (DOTAP) (see, for example, WO 98/07408), lysinylphosphatidylethanola-mine (L-PE), lipopolyarrines such as lipospermine, N-(2-hydroxy-ethyl)N,N-d-imethyl-2,3-bis(dodecyloxy)-1-propan-aminium bromide, dimethyl dioctadecyl ammonium bromide (DDAB), dioleoylphosphatidyl ethanolamine (DOPE), dioleoylphosphatidyl choline (DOPC), N(1,2,3-dioleyloxy) propyl-N,N,N-triethylanunonium (DOTMA), DOSPA, DMRIE, GL-67, GL-89, Lipofectin, and Lipofectamine (Thiery et al. (1997) *Gene Ther.* 4:226-237; Felgner et al., *Annals New York Acad. Sci.* 772:126-139, 1995; Eastman et al., *Hum. Gene Ther.* 8:765-7.73, 1997). Polynucleotide/lipid formulations described in U.S. Pat. No. 5,858,784 can also be used in the methods described herein. Many of these lipids are commercially available from, for example, Boehringer-Mannheim, and Avanti Polar Lipids (Birmingham, Ala.). Also encompassed are the cationic phospholipids found in U.S. Pat. Nos. 5,264,618, 5,223,263 and 5,459,127. Other suitable phospholipids which may be used include phosphatidylcholine, phosphatidylserine, phosphatidylethanolamine, sphingomyelin, phosphatidylinositol, and the like. Cholesterol may also be included.

Viral Delivery

A preparation that includes units of a viral delivery system can be delivered to heart cells of a subject by any of a variety of methods.

For instance, a pharmaceutical preparation of the viral delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054-3057).

In one exemplary implementation, the preparation is directly injected into heart tissue. U.S. Ser. No. 10/914,829 describes a protocol for direct injection. Direct injection or application of a viral vector into the myocardium can restrict expression of the transferred genes to the heart (Gutzman et al, 1993, *Cric. Res.* 73: 1202-7; French et al., 1994, *Circulation.* 90:2414-24).

In another exemplary implementation, the preparation is introduced into the lumen of one or more coronary arteries. Passage of blood out of the coronary arteries can be restricted. The preparation can be delivered antegrade and allowed to reside in the arteries for between one to five minutes, e.g., between one to three minutes.

Non-viral vehicles may be delivered by similar methods.

Exemplary Stents

A stent can be coated with or can contain an agent that decreases phosphatase activity, e.g., an agent described herein. Methods for preparing stents (both biodegradable and non-biodegradable) for delivering a therapeutic agent are well known (see, e.g., U.S. Pat. Nos. 5,163,952, 5,304,121, 6,391,052, 6,387,124, 6,379,382, and 6,358,556, 6,605,110, 6,605,114, 6,572,645, 6,569,194, 6,545,748, 6,541,116, 6,527,801, 6,506,437). In one embodiment, a stent is coated with a therapeutic agent, e.g., an agent described herein, such as a nucleic acid that decreases phosphatase activity, using techniques known in the art.

In one embodiment, the stent is a stainless steel stent or nytinol mesh like devices. For example, a stent can be delivered into the coronary artery on a catheter during a PCI procedure (percutaneous coronary intervention). A stent can be deployed in the artery by either expansion by a balloon or by a self expanding delivery design. Exemplary commercially available stents include Gianturco-Roubin Stents (e.g., from Cook Cardiology), Multilink, Duet, Tetra, Penta, Zeta Stents (e.g., from Guidant); Nir, Wall Stents, Taxus (e.g., from SCIMED/Boston Scientific), GFX/S series Stents (e.g., from Medtronic/AVE), velocity and Cypher stents (e.g., from Johnson & Johnson/Cordis).

For example, a stent can be coated with a polymeric cation that can mediate nucleic acid condensation or compaction, e.g., as described in U.S. Pat. No. 6,596,699. Linear polycations such as poly-L-lysine, polyornithine, polyarginine and the like can be used. The polymers may be homopolymers, such as polylysine, polyomithine, or polyarginine, or may be heteropolymers, including random polymers formed of lysine, omithine, arginine and the like. More complex molecules may also be employed as polycations, such as branched or linear polyethylenimine and the like. Any of a variety of naturally occurring nucleic acid binding agents may be employed, such as spermine or spermidine, and are including within the definition of polycation. Protamine can similarly be employed, as can any of a variety of histones. Polyamidoamine dendrimers may similarly be employed, wherein terminal amino groups bind the nucleic acid by electrostatic means, resulting in positively charged condensates. The polycation may be specifically modified to provide optimal characteristics to form the desired condensate. For example, a repeating lysine chain of 18 residues followed by a tryptophan and an alkylated cysteine residue has been reported to form condensates with properties at least equal to polylysine (McKenzie et al., *J. Peptide Res.* 54:311-318 (1999)). In general, the polycation is positively charged, and has a net positive charge at about pH 6 to about 8 or has more than about five positively charged residues. The polycation has a higher number of positive charges compared to the number of negative charges. A polycation includes natural nucleic acid-binding proteins and recombinant nucleic acid-binding protein, such as homo- or hetero-polymers of amino acids or synthetic compounds that bind to one or more nucleic acid sequences found within natural or recombinant nucleic acid molecules and results in nucleic acid condensation.

An additional method of coating a therapeutic agent, such as a nucleic acid, onto a medical device, such as a stent, involves coating the medical device with a swellable hydrogel polymer as described, e.g., in U.S. Pat. No. 5,674,192 or 6,409,716. The hydrogel coating is characterized by the ability to incorporate a substantial amount of the nucleic acid, typically in aqueous solution form, and is swellable such that the aqueous solution can be effectively squeezed out of the coating when pressure is applied, e.g., by inflation or expansion of the stent. Administration of the drug in this way enables the drug to be site-specific, such that release of high concentrations can be limited to direct application to the affected tissue. The stent may also be coated with a viral particle that contains the nucleic acid.

Other methods of coupling a therapeutic agent, such as a nucleic acid, to a stent or other medical device are known in the art, see for example, U.S. Pat. No. 6,024,918, U.S. Pat. No. 6,506,408; U.S. Pat. No. 5,932,299.

In some embodiments, a stent described herein, in addition to being coated with, or containing, an agent that decreases phosphatase activity, can also be coated with a second therapeutic agent. For example, the stent can also contain one or more of: rapamycin, taxol and actinomycin-D, a thrombin inhibitor, an anti-thrombogenic agent, a thrombolytic agent, a fibrinolytic agent, a vasospasm inhibitor, a calcium channel blocker, a vasodilator, an antihypertensive agent, an antimicrobial agent, an antibiotic, an inhibitor of surface glycoprotein receptors, an anti-platelet agent, an anti-mitotic, a microtubule inhibitor, an anti-secretory agent, an actin inhibitor, a remodeling inhibitor, an antisense nucleotide, an anti-metabolite, an anti-proliferative, an anticancer chemotherapeutic agent, an anti-inflammatory steroid or non-steroidal anti-inflammatory agent, an immunosuppressive agent, a growth hormone antagonist, a growth factor, a dopamine agonist, a radiotherapeutic agent, a peptide, a protein, an enzyme, an extracellular matrix component, a free radical scavenger, a chelator, an antioxidant, an anti-polymerase, an antiviral agent, a photodynamic therapy agent, and a gene therapy agent.

Evaluation of Treatment

A treatment can be evaluated by assessing the effect of the treatment on a parameter related to cardiac function or cardiac cellular function, e.g., contractility. For example, SR $Ca^{2+}$ ATPase activity or intracellular $Ca^{2+}$ concentration can be measured, using the methods described above. Furthermore, force generation by hearts or heart tissue can be measured using methods described in Strauss et al., *Am. J Physiol.*, 262:1437-45, 1992.

A treatment can also be evaluated by its effect on a subject, e.g., according to parameters that one skilled in the art of treatment would recognize as relevant for the particular treatment. For example, in treating heart failure, exemplary parameters may relate to cardiac and/or pulmonary function. Cardiac parameters include pulse, EKG signals, lumen loss, heart rate, heart contractility, ventricular function, e.g., left ventricular end-diastolic pressure (LVEDP), left ventricular systolic pressure (LVSP), $Ca^{2+}$ metabolism, e.g., intracellular $Ca^{2+}$ concentration or peak or resting $Ca^{2+}$, force generation, relaxation and pressure of the heart, a force frequency relationship, cardiocyte survival or apoptosis or ion channel activity, e.g., sodium calcium exchange, sodium channel activity, calcium channel activity, sodium potassium ATPase pump activity, activity of myosin heavy chain, troponin I, troponin C, troponin T, tropomyosin, actin, myosin light chain kinase, myosin light chain 1, myosin light chain 2 or myosin light chain 3, IGF-1 receptor, PI3 kinase, AKT kinase, sodium-calcium exchanger, calcium channel (L and T), calsequestrin or calreticulin. The evaluation can include performing angiography (e.g., quantitative angiography) and/or intravascular ultrasound (IVUS), e.g., before, after, or during the treatment.

Propagation of Heart Cells

A heart cell culture can be obtained by allowing heart cells to migrate out of fragments of heart tissue adhering to a suitable substrate (e.g., a culture dish) or by disaggregating the tissue, e.g., mechanically or enzymatically to produce a suspension of heart cells. For example, the enzymes trypsin, collage nase, elastase, hyaluronidase, DNase, pronase, dispase, or various combinations thereof can be used. Trypsin and pronase give the most complete disaggregation but may damage the cells. Collagenase and dispase give a less complete disagregation but are less harmful. Methods for isolating tissue (e.g., heart tissue) and the disaggregation of tissue to obtain cells (e.g., heart cells) are described in Freshney R. I., Culture of Animal Cells, A Manual of Basic Technique, Third Edition, 1994.

Nucleic Acid Inhibitors

A modulator of phosphatase activity can be a nucleic acid, such as a siRNA, anti-sense RNA, triple-helix forming nucleic acid, or a ribozyme, which can decreases the expression of a phosphatase, e.g., a type 1 phosphatase.

For example, gene expression can be modified by gene silencing using double-strand RNA (Sharp (1999) *Genes and Development* 13: 139-141). RNAi, otherwise known as double-stranded RNA interference (dsRNAi) or small interfering RNA (siRNA), has been extensively documented in a number of organisms, including mammalian cells, the nematode *C. elegans* (Fire, A., et al, *Nature,* 391, 806-811, 1998).

dsRNA can be delivered to cells or to an organism to antagonize a phosphatase. For example, a dsRNA that is complementary to a phosphatase coding nucleic acid can silence protein expression of the phosphatase, e.g., a type 1 phosphatase. The dsRNA can include a region that is complementary to a coding region of a phosphatase, e.g., a 5' coding region, a region encoding a phosphatase core domain, a 3' coding region, or a non-coding region, e.g., a 5' or 3' untranslated region. dsRNA can be produced, e.g., by transcribing a cassette (in vitro or in vivo) in both directions, for example, by including a T7 promoter on either side of the cassette. The insert in the cassette is selected so that it includes a sequence complementary to the phosphatase-coding nucleic acid. The sequence need not be full length, for example, an exon, or between 19-50 nucleotides or 50-200 nucleotides. The sequence can be from the 5' half of the transcript, e.g., within 1000, 600, 400, or 300 nucleotides of the ATG. See also, the HISCRIBE™ RNAi Transcription Kit (New England Biolabs, Massachusetts) and Fire, A. (1999) *Trends Genet.* 15, 358-363. dsRNA can be digested into smaller fragments. See, e.g., US Patent Application 2002-0086356 and 2003-0084471.

In one embodiment, an siRNA is used. siRNAs are small double stranded RNAs dsRNAs) that optionally include overhangs. For example, the duplex region is about 18 to 25 nucleotides in length, e.g., about 19, 20, 21, 22, 23, or 24 nucleotides in length. Typically, the siRNA sequences are exactly complementary to the target mRNA.

"Ribozymes" are enzymatic RNA molecules which cleave at specific sites in RNA. Ribozymes that can specifically cleave nucleic acids that encode or that are required for the expression of phosphatase, e.g., type 1 phosphatases, may be designed according to well-known methods.

Artificial Transcription Factors

Artificial transcription factors, such as chimeric zinc finger proteins, can be engineered to interact with a sequence in or near a gene encoding a phosphatase inhibitor or a phosphatase, e.g., at a site in the a promoter or enhancer of the gene, e.g., within 1000, 700, 500, or 200 nucleotides of the mRNA start site, or within 50, 20, 10 nucleotides of a chromatin accessible site in the gene. See, e.g., U.S. Pat. No. 6,785,613. The artificial transcription factor can be designed to activate expression of the gene in the case where the gene encodes a phosphatase inhibitor (e.g., I-1), or to repression expression of the gene, e.g., in the case where the gene encodes a phosphatase.

The artificial transcription factor can be designed or selected from a library. For example, the artificial transcription factor can be prepared by selection in vitro (e.g., using phage display, U.S. Pat. No. 6,534,261) or in vivo, or by design based on a recognition code (see, e.g., WO 00/42219 and U.S. Pat. No. 6,511,808). See, e.g., Rebar et al. (1996) *Methods Enymol* 267:129; Greisman and Pabo (1997) *Science* 275:657; Isalan et al. (2001) *Nat. Biotechnol* 19:656; and Wu et al. (1995) *Proc. Nat. Acad. Sci.* USA 92:344 for, among other things, methods for creating libraries of varied zinc finger domains.

Optionally, the zinc finger protein can be fused to a transcriptional regulatory domain, e.g., an activation domain to activate transcription or a repression domain to repress transcription. The zinc finger protein can itself be encoded by a heterologous nucleic acid that is delivered to a cell or the protein itself can be delivered to a cell (see, e.g., U.S. Pat. No. 6,534,261. The heterologous nucleic acid that includes a sequence encoding the zinc finger protein can be operably linked to an inducible promoter, e.g., to enable fine control of the level of the zinc finger protein in the cell.

Administration

An agent that modulates phosphatase activity, e.g., an agent described herein, can be administered to a subject by standard methods. For example, the agent can be administered by any of a number of different routes including intravenous, intradermal, subcutaneous, oral (e.g., inhalation or ingestion), transdermal (topical), and transmucosal. In one embodiment, the agent is administered by injection, e.g., intra-arterially, intramuscularly, or intravenously.

The agent, e.g., a nucleic acid molecule encoding a phosphatase inhibitor, polypeptide, fragments or analog, modulators (e.g., organic compounds and antibodies (also referred to herein as "active compounds") can be incorporated into pharmaceutical compositions suitable for administration to a subject, e.g., a human. Such compositions typically include the polypeptide, nucleic acid molecule, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and anti-fungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an agent described herein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

In a preferred embodiment, the pharmaceutical composition is injected into an affected vessel, e.g., an artery, or an organ, e.g., the heart.

Small Molecule Agents

Small molecule agents that modulate phosphatase activity, e.g., inhibit phosphatase activity can be identified by a small molecule screen. One or more candidate molecules can be contacted to a phosphatase and evaluated to determine if the candidate molecule interacts with the phosphatase or modulates enzymatic activity of the phosphatase. The contacting can be effected in vitro or in vivo. In vitro assays, for example, can use highly purified components, e.g., using a recombinant protein that has phosphatase activity, e.g., at least a catalytic fragment of a human phosphatase. Phosphatase enzymatic activity can be evaluated in vitro.

For example, protein phosphatase 1 activity can be assayed as described (Endo, S., et al. (1996) *Biochemistry* 35, 5220-5228) in a 30-μl reaction mixture containing 50 mM Tris-HCl (pH 7.4), 1 mM DTT, 0.5 mM $MnCl_2$, 10 μM [$^{32}P$]phosphorylase a, and 0.5 μg/ml PP1. The reaction is initiated by the addition of 1 μl of PP1 to 20 μl of assay mixture containing the rest of the assay components. After 20 min at 30° C. the reaction is terminated by adding 10 μl of 50% trichloroacetic acid to the assay mixture. The assay mixture is then cooled on ice and centrifuged. A 20 μl aliquot from the supernatant was spotted onto filter paper and placed in a scintillation counter to determine the amount of released [$^{32}P$]$P_i$. [$^{32}P$]Phosphorylase a used for PP1 assays was prepared at 30° C. for 30 min as described. [$^{32}P$]Phosphorylase a was dialyzed in 50 mM Tris-HCl, pH 7.4, 1 mM EDTA, 1 mM DTT and stored frozen at −80° C. until used (see also Huang et al. *Proc Natl Acad Sci USA*. 2000 May 23; 97 (11):5824-9).

In many drug screening programs which test libraries of therapeutic compounds and natural extracts, high throughput assays are desirable in order to maximize the number of test compounds surveyed in a given period of time.

The efficacy of a test compound can be assessed by generating dose response curves from data obtained using various concentrations of the test compounds. Moreover, a control assay can also be performed to provide a baseline for comparison. In the control assay, the heart cell is incubated in the absence of a test compounds.

A "compound" or "test compound" can be any chemical compound, for example, a macromolecule (e.g., a polypeptide, a protein complex, or a nucleic acid) or a small molecule (e.g., an amino acid, a nucleotide, an organic or inorganic compound). The test compound can have a formula weight of less than about 10,000 grams per mole, less than 5,000 grams per mole, less than 1,000 grams per mole, or less than about 500 grams per mole. The test compound can be naturally occurring (e.g., a herb or a nature product), synthetic, or both. Examples of macromolecules are proteins, protein complexes, and glycoproteins, nucleic acids, e.g., DNA, RNA and PNA (peptide nucleic acid). Examples of small molecules are peptides, peptidomimetics (e.g., peptoids), amino acids, amino acid analogs, polynucleotides, polynucleotide analogs, nucleotides, nucleotide analogs, organic or inorganic compounds e.g., heteroorganic or organometallic compounds. A test compound can be the only substance assayed by the method described herein. Alternatively, a collection of test compounds can be assayed either consecutively or concurrently The test compounds can be obtained, for example, as described above (e.g., based on information about an agonist) or using any of the numerous combinatorial library method. Some exemplary libraries include: biological libraries; peptoid libraries (libraries of molecules having the functionalities of peptides, but with a novel, non-peptide backbone which are resistant to enzymatic degradation but which nevertheless remain bioactive (see, e.g., Zuckermann, R. N. et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. These approaches can be used, for example, to produce peptide, non-peptide oligomer or small molecule libraries of compounds (see, e.g., Lam (1997) *Anticancer Drug Des.* 12:145).

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14 (3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like). Additional examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

A biological library can includes polymer that can be encoded by nucleic acid. Such encoded polymers include polypeptides and functional nucleic acids (such as nucleic acid aptamers (DNA, RNA), double stranded RNAs (e.g., RNAi), ribozymes, and so forth). The biological libraries and non-biological libraries can be used to generate peptide libraries. Another example of a biological library is a library of dsRNAs (e.g., siRNAs), or precursors thereof. A library of nucleic acids that can be processed or transcribed to produce double-stranded RNAs (e.g., siRNAs) is also featured.

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.). In many cases, a high throughput screening approach to a library of test compounds includes one or more assays, e.g., a combination of assays. Information from each assay can be stored in a database, e.g., to identify candidate compounds that can serve as leads for optimized or improved compounds, and to identify SARs.

The following examples are provided as a further description of the invention, and to illustrate but not limit the invention.

EXAMPLES

Example 1

I-1 and its Phosphorylation in Failing Human Hearts

To examine the levels and the phosphorylation state of I-1 in failing human hearts, the levels of I-1 were compared in biopsies from nine non-failing and ten failing human hearts, in which the primary diagnosis was dilated cardiomyopathy (IDC). To control for equal loading of protein, the data were normalized to calsequestrin protein levels, as the levels of this SR protein were similar between failing and non-failing samples (FIG. 1A). Total I-1 protein levels were not different between donor and failing hearts but its degree of phosphorylation was significantly reduced (~60%) in failing hearts (FIG. 1B), indicating that I-1 was predominantly inactive and thus, incapable of inhibiting PP1 activity in the failing human heart. The decreased I-1 phosphorylation may reflect impaired β-adrenergic signaling and decreased PKA activation due to reduced cAMP levels in failing (5.8±0.7 pmol/mg, n=9) compared to donor (10.9±1.3 pmol/mg, n=10, p<0.05) hearts.

Example 2

Inhibition of PP1 by a Constitutively Active I-1 Enhances Contractile Responses to β-Agonists in Failing Human Cardiomyocytes I-1 deficient mouse hearts show decreased contractile parameters. Further, in some cases of human heart failure, PP1 activity is increased. This increase may, at least partly, be due to inactivation or dephosphorylation of I-1, leading to depressed function. Thus, increasing I-1's activity can be beneficial in restoring the attenuated β-adrenergic responsiveness in failing human cardiomyocytes.

Figure 2:
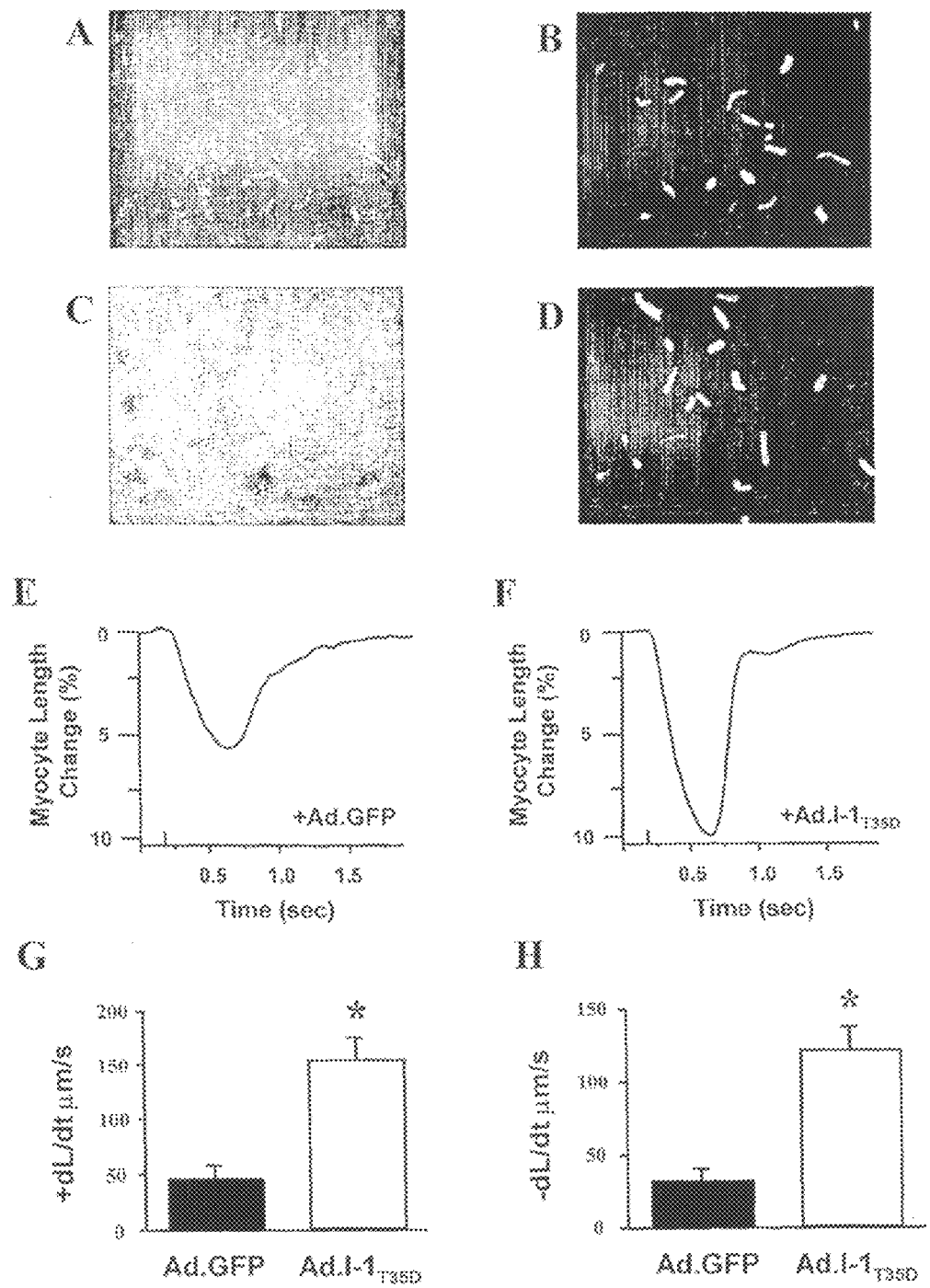
FIGS. 2A, 2B, 2C, 2D, 2E, 2F, 2G, and 2H show the results of expressing a constitutively active I-1 protein in cardiomyocytes from failing human hearts: (A-D) Isolated failing human myocytes expressing either (Top) β-galactosidase-GFP (Control) or (Bottom) I-1$_{T35D}$-GFP were visualized with direct light (left panels) or fluorescent light (right panels). Successfully infected cells appear green (right panels). Representative traces of cardiomyocyte cell shortening in (E) Ad.GFP and (F) Ad.I-1$_{T35D}$ infected cells in response to a maximal concentration of isoproterenol. Quantitation of the rates of (G) cell shortening and (H) re-lengthening in Ad.GFP and Ad.I-1$_{T35D}$ infected cells under 100 nM isoproterenol. * indicates $P<0.05$. Values are averages of at least 8-12 cells from 3-5 human hearts.

Adenoviral-mediated expression of a constitutively active I-1 protein (I-1$_{T35D}$) was used in myocytes isolated from human failing hearts (del Monte F, et al., *Circulation.* 1999; 100:2308-11). The design of the I-1$_{T35D}$ construct entailed truncation of the I-1 cDNA to encode for the first 65 amino acids and introduction of nucleotide changes to replace the PKA phosphorylation site (ACC:Thr$^{35}$) with aspartic acid (GAC:D), resulting in a constitutively active inhibitor (Endo, S., et al., *Biochemistry.* 1996; 35:5220-8). In parallel studies, cardiomyocytes were infected with an adenovirus encoding for β-galactosidase to serve as controls. Both constructs also contained sequences encoding for the green fluorescent protein (GFP), which served as a marker of transfection (FIGS. 2B & D).

Failing human cardiomyocytes infected with either β-gal or I-1$_{T35D}$ constructs exhibited similar contractile function under basal conditions. However, in response to isoproterenol (100 nM) myocytes infected with I-1$_{T35D}$ displayed significantly increased myocyte shortening (FIGS. 2E & F), rates of cell shortening (FIG. 2G) and re-lengthening (FIG. 2H) and a lower time constant for relaxation, tau (τ) (I-1$_{T35D}$: 0.16±0.05, n=8 vs. GFP: 0.37±0.09, n=10, p<0.05), compared to controls. Additionally, the time to 50% decay of the calcium signal (I-1$_{T35D}$: 0.33±0.06, n=8 vs. GFP: 0.52±0.06, sec, n=10, p<0.05) and τ for the calcium signal decay (I-1$_{T35D}$: 0.36±0.10, n=8 vs. GFP: 0.70±0.09, n=10, p<0.05) were accelerated in the I-1 transfected cells, compared to controls.

Accordingly, expression of a protein that inhibits phosphatase is effective for decreasing PP1 activity, an activity which is reported to be elevated in human heart failure. In addition, these results indicate that inhibition of PP1 activity by I-1$_{T35D}$ significantly improves the β-adrenergic responsiveness in the failing human heart.

Example 3

Percutaneous Antegrade Intracoronary Gene Transfer with Concomitant Coronary Vein Blockade (CVB) can be Used to Deliver Genes to Heart Tissue Different serotypes of AAV were tested for their ability to deliver an exogenous gene to the heart. AAV6 has found to have some surprising and unexpected properties relative to other AAVs. AAV6 conferred the fastest gene expression, as well as the most specific and efficient expression in the heart (data not shown). Other AAVs, however, may be useful for other applications, e.g. ones in which a different course of expression is desired in heart tissue.

Percutaneous antegrade intracoronary gene transfer with concomitant coronary vein blockade (CVB) was performed in both sheep and swine models. The left anterior descending artery (LAD) or the left circumflex artery (LCX) was cannulated and occluded with a standard angioplasty balloon. One-minute ischemic preconditioning in both the LAD and the LCX distribution (by blockade of the LAD and the LCX) was performed to allow increased viral dwell time. Following the preconditioning protocol, the great coronary vein (GCV) or one of its branches was cannulated and temporarily occluded with a standard wedge balloon catheter. CVB was performed globally, implying occlusion of the proximal GCV and thus occluding venous drainage in both the LAD and LCX distribution, or selectively, in which case the anterior interventricular vein (AIV) was occluded during LAD delivery and similarly, the ostium of the middle cardiac vein (MCV) was occluded during LCX delivery. With both the arterial and the venous balloons inflated, percutaneous antegrade intracoronary gene transfer was performed by injection through the center lumen of the inflated angioplasty balloon with an adeno-associated virus carrying β-galactosidase (AAV6. β-gal) (n=5).

Twelve weeks following gene transfer with AAV6.CMV. β-gal, myocardial sections of 10 μm were obtained from the septal, anterior, left lateral, posterior, and right ventricular walls. These sections were fixed with a phosphate-buffered solution (PBS), containing 0.5% glutaraldehyde for 30 minutes, and then in PBS with 30% sucrose for 30 minutes. The sections were then incubated overnight in a solution containing 5-bromo-4-chloro-3-indolyl α-D-galactopyranoside (X-gal). The results indicated an extensive transfer of β galactosidase throughout the myocardium (data not shown). Therefore, antegrade transduction of AAV6.CMV.β-gal at a concentration of $5 \times 10^{14}$ genomes/ml with the global CVB resulted in a significant gene expression in the targeted myocardium, demonstrating feasibility and safety in a large animal model.

Gene transfer using coronary venous occlusion was further confirmed. In brief, a reporter gene and a gene encoding SERC2A was successfully transferred in pigs, relying upon the AAV6.CMV construct (data not shown).

Example 4

Expression of the Active Inhibitor-1 In Vivo Enhances Cardiac Function

To determine the long term in vivo effects of decreased protein phosphatase 1 activity, a constitutively active, truncated inhibitor-1 (I-T35D; AA 1-65) was expressed in a cardiomyocyte restricted manner. This form of inhibitor-1 was chosen because it specifically inhibits protein phosphatase 1, albeit at higher concentration than the native phosphorylated inhibitor (Endo, S., et al., *Biochemistry.* 1996; 35:5220-8) and, more saliently, it remains active in heart failure, where the β-adrenergic receptor signaling axis is down-regulated (Bristow, M. R., et al., *N Engl J. Med.* 1982; 307:205-11).

A 5.6-kb transgene, consisting of the a-MHC promoter followed by the mouse I-T35D (AA 1-65) cDNA, and the simian virus 40 polyadenylation site was constructed, restricted, gel purified and then microinjected into the pronuclei of one-cell inbred FVB/N embryos. The TG mice were handled according to protocols approved by the Institutional Animal Care and Use Committees at the University of Cincinnati.

Three transgenic lines were obtained with similar levels of I-T35D expression (25-fold compared to WTs). In vivo cardiac function was assessed by non-invasive echocardiography, as previously described (Hoit, B. D., et al., *Circ. Res.* 1995; 77:632-7). Transgenic and wild-type mice were anesthetized with Avertin 2.5% (10 µ/gram body weight) for each experiment, and cardiac function was assessed under blinded conditions. The student's t-test and ANOVA, followed by the Neuman-Keuls t-test, were used to determine the statistical difference between groups. Data was presented as mean±standard error. For each experiment, statistical significance was established at a P value <0.05. Statistical analysis was carried out on Prism 3.0.

The three lines, along with age and gender matched wild-types (WT), were examined by M-mode and Doppler echocardiography. At 3 months of age, an enhancement in the velocity of circumferential fiber shortening (Vcf) was observed (TG: 7.91±0.31, vs. WT: 6.28±0.54, circ/sec; P<0.05) and the ejection time was abbreviated (TG: 56.77±1.81, vs. WT: 64.0±2.07, msec; P<0.05) in active inhibitor-1 transgenic hearts (n=14) compared to wild-types (n=5). Moreover, cardiac function was similarly increased at 6 months of age and longevity studies (19 WTs and 19 TGs) indicated no evidence of sudden death, while Kaplan-Meier survival analysis (up to 2 years of age) revealed no significant differences in mortality rates. Subsequent studies were carried out with one of the transgenic lines (Line C). There was a significant decrease (15%) in cardiac protein phosphatase 1 activity (FIG. 3A), and no compensatory changes in either overall PP1 catalytic subunit protein level or PP2A activity compared to WTs (data not shown).

PP1 activity was examined using $^{32}$P-labeled glycogen phosphorylase a as a substrate (Carr, A. N., et al., *Mol. Cell Biol.* 2002; 22:4124-35; Suzuki, Y., et al., *Mol. Cell Biol.* 2001; 21:2683-94) in the presence of 4 nM okadaic acid, at concentrations that selectively inhibit type 2A phosphatase, and EDTA (0.5 mM), an inhibitor of type 2B phosphatase. The assays were conducted under conditions where no more than 15% of the substrate was utilized to assure linearity of the reaction.

In vivo cardiac function was examined using the Langendorff perfusion system as previously described (Sato, Y., et al., *J. Biol Chem.* 1998; 273:28470-7). The heart rate and the maximal first derivatives of intraventricular pressure (±dP/dt) were continuously calculated. For cell function, calcium tolerant cardiomyocytes were isolated and a subset was loaded with Fura-2-AM (Zhao, W., et al., *Cardiovasc Res.* 2003; 57:71-81). Basal and isoproterenol stimulated contractile parameters and $Ca^{2+}$ transients were determined using a video-edged detection system. Cells were paced at 0.5 Hz Data were analyzed by Felix computer software (Photon Technology International, Lawrenceville, N.J., USA).

Figure 3:
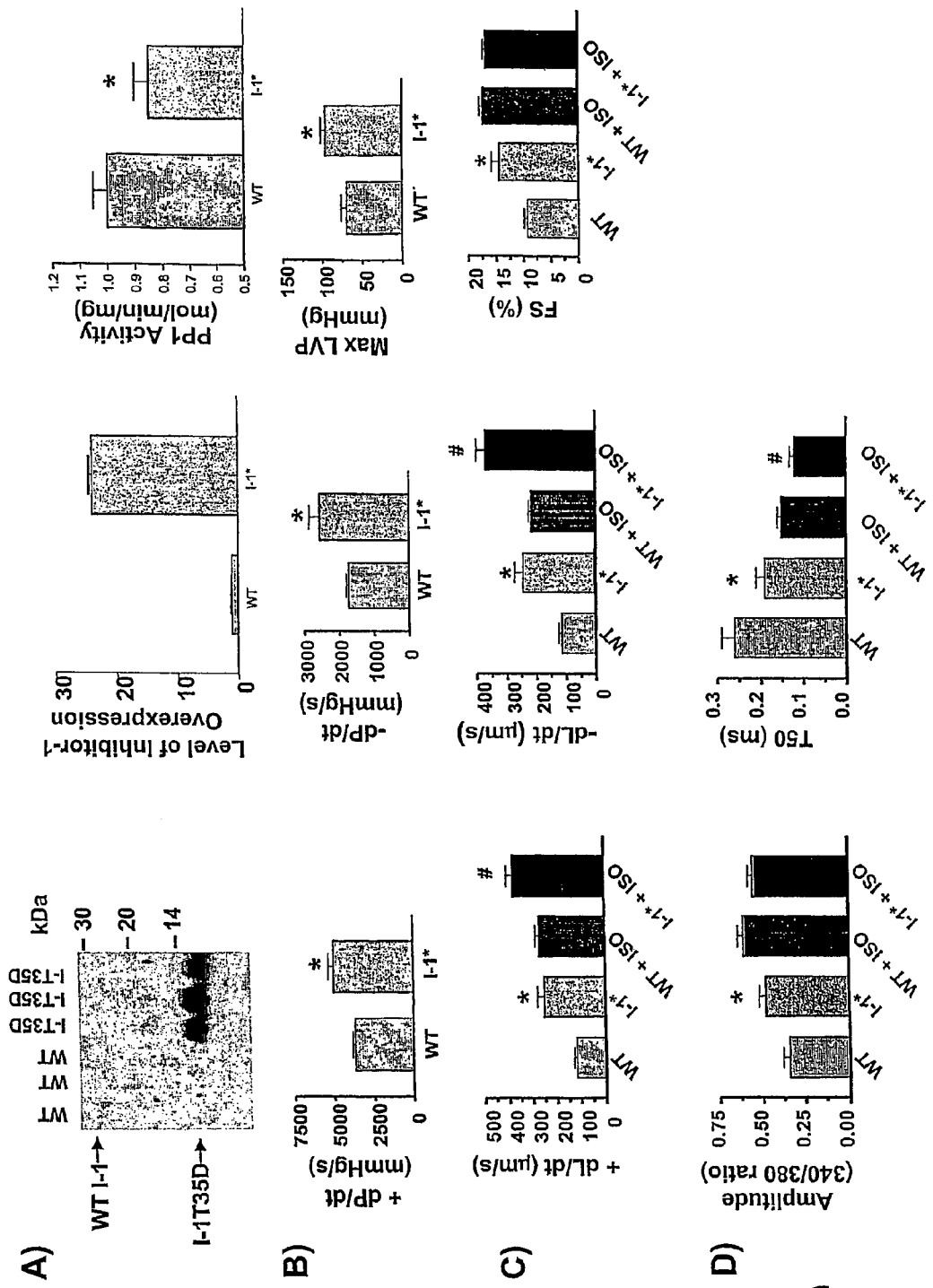
FIG. 3A shows an immunoblot depicting active inhibitor-1 protein expressed at ~25-fold higher levels than the endogenous inhibitor-1, resulting in a 15% decrease in the type 1 phosphatase activity. *$P<0.05$, n=6 per group.
FIG. 3B shows, in bar graph form, pressure measurements from the Langendorff ex vivo assessment of cardiac contractility in 3 month old I-1* and wild-types (WT), indicating that inhibitor-1 hearts exhibited significantly enhanced rates of pressure development (±dP/dt).
FIG. 3C shows, in bar graph form, measurements of myocyte shortening rates.
FIG. 3D shows, in bar graph form, measurements of the amplitude of calcium transients. *$P<0.05$ vs. WT and #$P<0.05$ vs. WT+ISO, n>30 cardiomyocytes from 6-8 hearts per group.

The Langendorff perfused hearts, which represent a system free from neurohormonal or hemodynamic influences, also indicated enhanced intrinsic cardiac contractility. In active inhibitor-1 expressing hearts, the maximal left ventricular pressure was increased (23%) and the +dP/dt and –dP/dt were augmented by 39% and 36%, respectively, relative to wild-type cohorts (FIG. 3B). Furthermore, isolated calcium tolerant cardiomyocytes, exhibited increases (56%) in fractional shortening (FIG. 3C). Under basal conditions, the +dL/dt and –dL/dt, as well as the degree of fractional shortening (% FS), were enhanced in the active inhibitor-1 expressing cardiomyocytes. Also, under isoproterenol stimulation (ISO), the +dL/dt and –dL/dt were enhanced. Rates of myocyte shortening (–dL/dt) and re-lengthening (+dL/dt) were also enhanced over 2-fold by active inhibitor-1 expression (FIG. 3C). The times to 50% peak and 50% relaxation were also significantly decreased. Furthermore, when cardiomyocytes were maximally stimulated with isoproterenol (100 nM), the rates of myocyte shortening (–dL/dt) and relengthening (+dL/dt) continued to be enhanced (FIG. 3C).

The alterations in mechanical parameters reflected similar enhancement in calcium cycling. Under basal conditions, both the amplitude and time to 50% decay ($T_{50}$) of the calcium transient were enhanced in active inhibitor-1 cardiomyocytes. Under isoproterenol (100 nM) stimulation, $T_{50}$ was also abbreviated. In effect, the amplitude of calcium transients was increased by (71%), reflecting enhanced SR calcium uptake and SR calcium load, and the time to 50% decay of the $Ca^{2+}$ signal ($T_{50}$) was reduced by (37%) (FIG. 3D), indicating enhanced SERCA2 function.

Of note, even under isoproterenol stimulation, the active inhibitor-1 cardiomyocytes continued to exhibit an abbreviated $T_{50}$, while the amplitude of the calcium transient was not different from wild-type cardiomyocytes, consistent with the mechanical parameters. These findings on enhanced basal contractility and augmented β-adrenergic responsiveness support the role of inhibitor-1 as a molecular inotrope. The example, thus, shows that mice with cardiac-specific expression of the active inhibitor-1 (I-1*) exhibit a decrease in cardiac type 1 phosphatase activity and an increase in cardiac contractility.

Example 5

Effect of Active Inhibitor-1 on $Ca^{2+}$ Handling Proteins and Glycogen Metabolism As described above, β-adrenergic receptor dependent protein phosphorylation of key regulatory phosphoproteins, such as phospholamban, the ryanodine receptor, troponin I and the L-type calcium channel, constitutes a critical regulatory mechanism, that governs $Ca^{2+}$-cycling and cardiac contractility. Thus, the expression (FIG. 4A) and phosphorylation levels (FIG. 4B) of these key substrates were investigated in the transgenic model described herein.

Quantitative immunoblotting was performed on cardiac homogenates, as previously described[11, 18]. Immunoprecipitation experiments were performed using protein G dynabeads (Dynal Bioctechnology Incorporated, Lake Success, N.Y.). Briefly, 50 µl of PP1a antibody (Santa Cruz Biotechnology, sc-6104) was conjugated to the magnetic protein G beads, using 0.2 M triethanoalamine and 20 mM dimethylpimedilate as described by the manufacturer. 500 µl of cardiac homogenate was incubated with the beads overnight, with constant rotational motion. The beads were washed with 5× with PBS plus 0.1% Tween20. Finally, the proteins bound to the PP1 antibody were eluted using 0.1 M citric acid (pH 2.8), and then separated on SDS-PAGE, blotted and probed, as described above.

It was first determined that there were no differences in β-adrenergic receptor density, in radioligand binding studies with $^{125}$I-iodocyanopindolol (data not shown). Radioligand binding studies were performed as described previously (McGraw, D W and Liggett, S B, *J. Biol. Chem.* 1997; 272: 7338-44). Briefly, mouse hearts were homogenized in buffer containing 5 mM Tris, 2 mM EDTA pH 7.4, benzamidine (5 µg/ml) and soybean typsin inhibitor (5 µg/ml). The homogenate was centrifuged at 40,000×g for 10 minutes at 4° C. The resulting pellets were resuspended in 10 volumes of homogenization buffer and centrifuged again. The pellet was resuspended in assay buffer (75 mM Tris, 12.5 mM $MgCl_2$, 2 mM EDTA, pH 7.4) and aliquots were then incubated in a total volume of 250 µl at room temperature, for 2 hours with ~400 pM $^{125}$I labeled iodocyanopindolol. Non-specific binding, was determined in the presence of 1 µM propranolol. To stop the reaction, cold wash buffer (10 mM Tris, pH 7.4) was added and vacuum filtration was performed through Whatman GF/C glass fiber filters.

Figure 4:
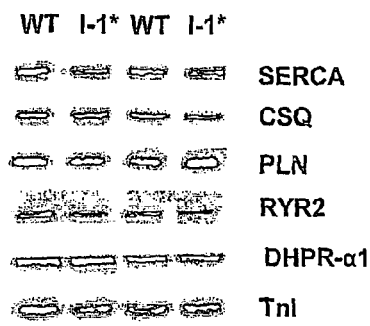
FIG. 4A shows an immunoblot (and a bar-graph quantitation of the same) depicting levels of SERCA2, phospholamban (PLN), calsequestrin (CSQ), the dihydropyridine receptor (DHPR), troponin I (TnI), and the ryanodine receptor (RYR2). *$P<0.5$, n=at least 5 hearts each for WTs and TGs.
FIG. 4B shows an immunoblot (and a bar-graph quantitation of the same) depicting the phosphorylation of phospholamban at both Ser16 and Thr17 in active inhibitor-1 hearts, as well as the phosphorylation of the ryanodine receptor and troponin I (mol Pi/mol RyR). *$P<0.05$, f=at least 5 hearts each for WTs and TGs.
FIG. 4C graphically depicts, in the top panel, the current-voltage relationship of WT vs. active inhibitor-1 cardiomyocytes. In the bottom panel, FIG. 4C graphically, in the bottom panel, depicts the calcium dependent inactivation kinetics of the L-type $Ca^{2+}$ channel in the I-1* OE cardiomyocytes (vs. wild-type). *$P<0.05$, n=5 hearts per group and at least 25 cardiomyocytes per group.
Figure 4:
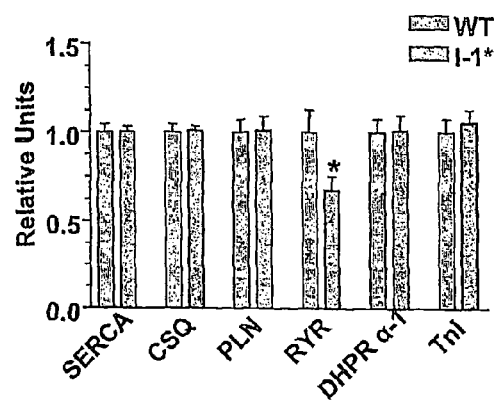
Figure 4:
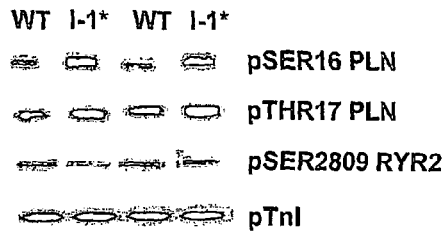
Figure 4:
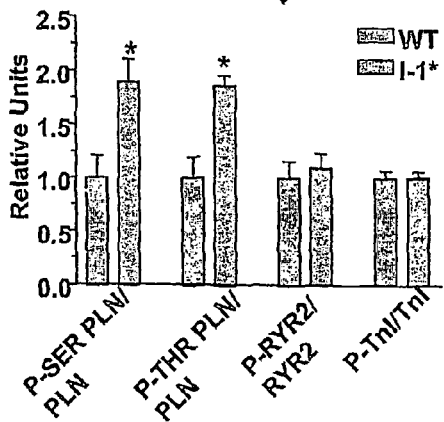
Figure 4:
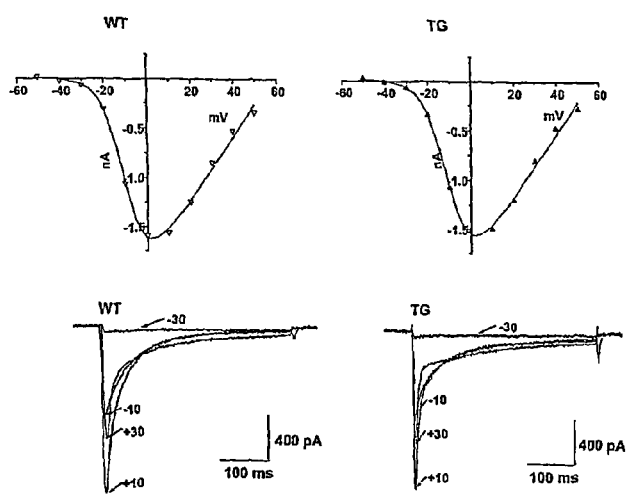

However, there was a prominent increase (~1.8-fold) in the phosphorylation level of phospholamban at both its cAMP dependent (Ser16) and $Ca^{2+}$ calmodulin dependent (Thr17) protein kinase sites, compared to wild-type hearts (FIG. 4B). Interestingly, the cardiac ryanodine receptor protein levels were decreased by ~30% (FIG. 4A), but there was no difference in the relative (mol Pi/mol RyR2) phosphorylation of this channel (FIG. 4B). This finding on ryanodine receptor phosphorylation was surprising, since both protein phosphatase 1 and protein phosphatase 2A have been shown to coimmunoprecipitate with the ryanodine receptor macromolecular complex. (Marx S O, et al., *Cell*. 2000; 101:365-76).

Examination of protein or phosphorylation levels of troponin I indicated no alterations in the active inhibitor-1 expressing hearts (FIG. 4B). Furthermore, there were no alterations of the L-type $Ca^{2+}$ channel protein level. Calcium tolerant cardiomyocytes were isolated and cells with clear cross striations and without spontaneous contractions were used for the measurement of L-type $Ca^{2+}$ current. Current recordings were obtained at constant voltage, and cell capacitance and $Ca^{2+}$ channel inactivation was determined (Bodi, I., et al., *J. Am. Coll. Cardiol.* 2003; 41:1611-22). The mean peak $Ca^{2+}$ current ($I_{Ca}$) and the steady-state inactivation of the current-voltage relationship (I-V) were similar between active inhibitor-1 expressing and wild-type myocytes. However, inactivation of $I_{Ca}$ was faster in the active inhibitor-1 transgenic cells than in wild-type cells (FIG. 4C), similar to previous observations in the phospholamban knock-out mice (Masak, H., et al., *Am. J. Physiol.* 1997; 272:H606-12).

Importantly, glycogen metabolism was investigated, and no significant difference was observed in glycogen synthase and glycogen phosphorylase activities between active inhibitor-1 expressing and wild-type hearts. Moreover, there was no difference in the overall glycogen accumulation in these hearts. Thus, expression of the active inhibitor-1 in the myocardium does not have significant effects on glycogen metabolism, consistent with previous findings on inhibitor-1 ablation, which did not alter glycogen metabolism in skeletal muscle (Scrimgeour, A G, et al., *J. Biol. Chem.* 1999; 274: 20949-52).

Example 6

The Active Inhibitor-1 Delays Functional Deterioration and Decompensated Cardiac Hypertrophy in Pressure-Overload To examine the hypothesis that the active inhibitor-1 expression, associated with enhanced $Ca^{2+}$ cycling, may be protective against cardiac remodeling induced by hemodynamic stress, we subjected the transgenic mice and isogenic wild-type cohorts were subjected to banding of the transverse aorta, followed by serial echocardiographic assessment at 6 and 12 weeks post banding (Kiriazis, H., et al., *Cardiovasc Res.* 2002; 53:372-81). Transverse aortic constriction on mice was performed, as previously described. (Kiriazis H., et al., *Cardiovasc Res.* 2002; 53:372-81). Briefly, 10 week old FVBN male wild-type and transgenic mice underwent banding of the transverse aorta, using a 27-gauge needle. Echocardiography was performed prior to banding and at various time points post-banding. At the termination point, trans-aortic gradients, as well as lung, liver, heart and body weight, were measured, and cardiac tissue was stored for subsequent histopathological analysis and biochemical studies.

While trans-aortic gradients were similar between these two groups (WT: 47.4±2.50; TG: 46.75±2.69, mmHg), active inhibitor-1 mice exhibited no decline in Vcfc, and an increase in the h/r (wall thickness/radius) ratio (FIG. 5A), suggesting maintained function and reduced wall-tension or stress, as determined by La Place's law. In contrast, WTs experienced a ~30% decline in $Vcf_c$ and significant increases in left-ventricular end-diastolic and end-systolic dimensions (P<0.05), indicating their progression to cardiac dilatation (FIG. 5A).

Pressure measurements were performed as previously described. (del Monte F., et al., *Circulation*. 2001; 104:1424-9). The time course of isovolumic relaxation (τ) was calculated using the equation: $P=P_o e^{-\tau} + P_B$, where P is the left ventricular isovolumic pressure, $P_o$ is pressure at the time of peak $-dP/dt$, and $P_B$ is residual pressure. For the pacing studies, an epicardial lead was placed at on atrial appendage connected to a stimulator (Grass Instruments, MA). In a subset of animals, multiple 0.7 mm piezoelectric crystals (Sonometrics Co., Canada) were placed over the surface of the left ventricle along the short axis of the ventricle at the level of the mitral valve to measure the inter-crystal distance. Left ventricular pressure-dimension loops were generated under different loading conditions by clamping the inferior vena cava. The end-systolic pressure-dimension relationship was obtained by producing a series of pressure dimension loops over a range of loading conditions and connecting the upper left hand corners of the individual pressure-dimension loops to generate the maximal slope.

Figure 5:
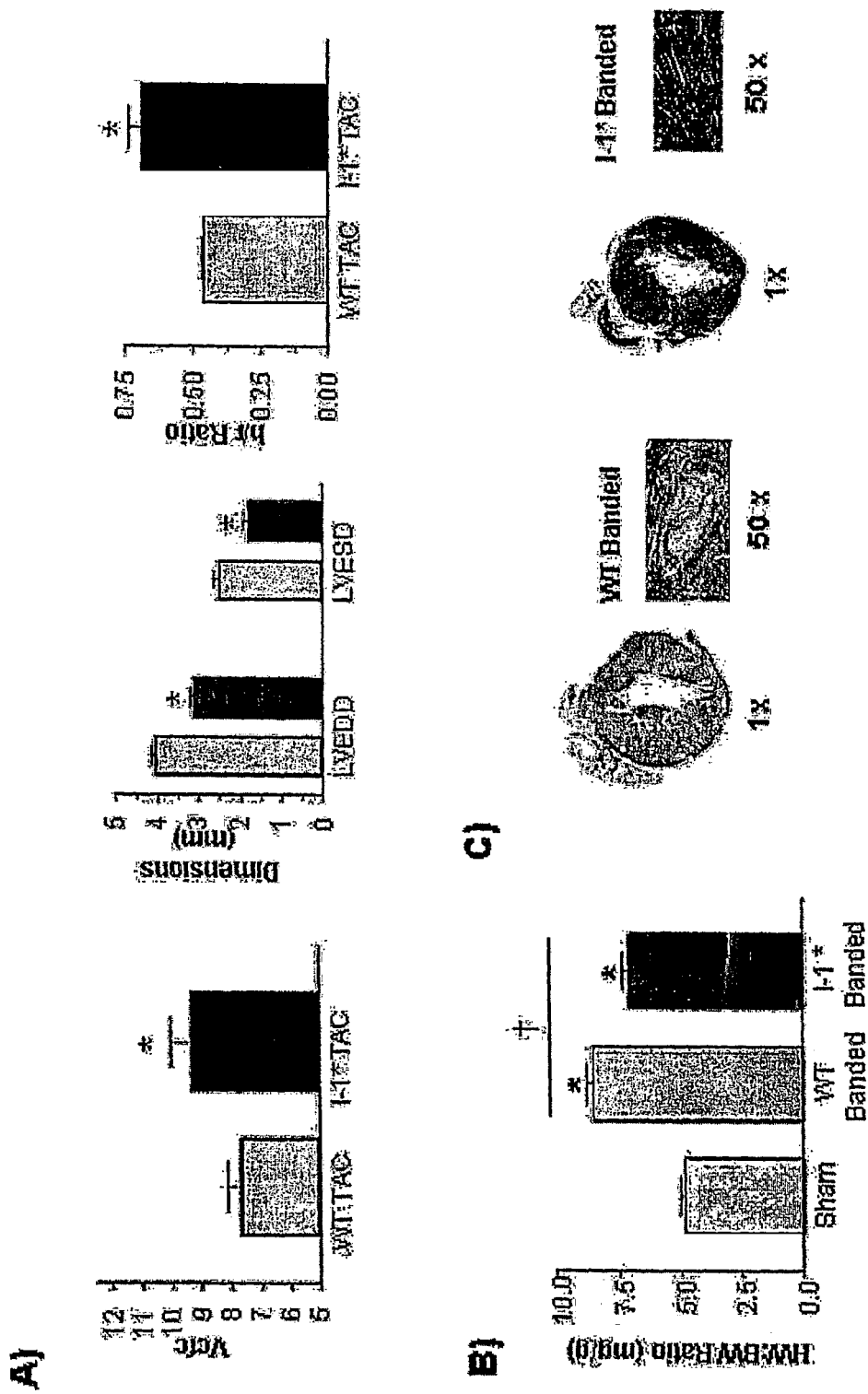
FIG. 5A shows, in bar-graph form, the results of echocardiographic assessment of wild-type vs. transgenic mice at 6 weeks post-aortic banding (Vcf$_c$, left ventricular end-systolic and end-diastolic dimensions, and h/r ratio). $P<0.05$, n=5 mice per group.
FIG. 5B shows, in bar-graph form, the results of gravimetric analysis of the wild-type vs. transgenic mice. *$P<0.05$ vs. Sham surgery group, † $P<0.05$ between WT-banded and I-1* banded hearts; n=4-5 per group.
FIG. 5C shows histograms showing the hearts of the wild-type vs. transgenic mice at the microscopic level.

At the termination point of the study (12 weeks), the heart to body weight ratio was increased by 78% in wild-types and 52% in the active inhibitor-1 mice, relative to sham controls (FIG. 5B). The frequency of lung-congestion was also much higher in wild-types (80%), compared to active inhibitor-banded mice (20%). Lung congestion was defined as a lung weight 2 standard deviations greater than the sham controls.

Figure 6:
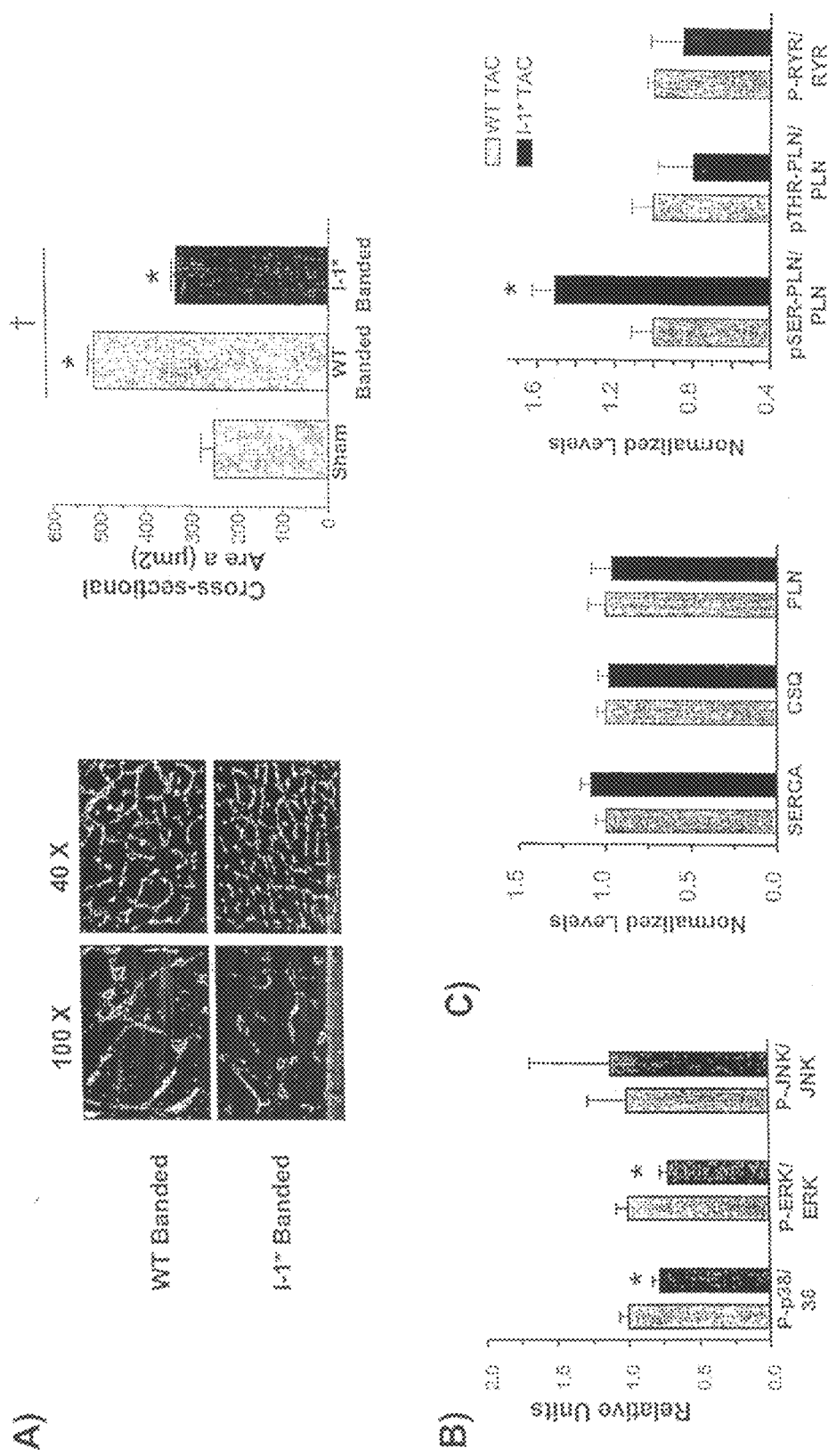
FIG. 6A shows, in the left panel, representative images of heart cross-sections from WT banded and I-1* banded hearts (100× and 40×). In the right panel.
FIG. 6B shows, in bar-graph form, the results of quantitative immunoblotting of MAP-kinase proteins. *P<0.05, n=4 mice per group.
FIG. 6C shows, in bar-graph form, the results of quantitative immunoblotting depicting the levels of Sarcoplasmic reticulum proteins (SERCA, calsequestrin (CSQ) and phospholamban (PLN)) and the levels of phosphorylation of phospholamban and ryanodine receptor. *P<0.05, n=4 mice per group.

Further examination of the hearts at the microscopic level, revealed increased interstitial and perivascular fibrosis in banded WT hearts (FIG. 5C)—with moderate to severe multifocal and perivascular fibrosis in the wild-type mice and moderate to mild fibrosis in the active inhibitor-1 hearts. Thus, Example 6 indicates that active inhibitor-1 expression protects mice subjected to aortic banding from cardiac functional deterioration and morphological deterioration. Histopathological studies with H&E, trichrome, PAS and TRITC-labeled wheat-germ agglutinin (Sigma Chemical Co., St. Louis, Mo., USA) for cardiomyocyte cross-sectional area were performed as previously described (Cohen, P., *Adv. Second Messenger Phosphoprotein Res.* 1990; 24:230-5). Specifically, for wheat germ agglutinin labeling of the cell wall, 40 or more cell cross-sectional areas (from multiple sections) were determined for each heart (n=3 hearts per group). Wheat germ agglutinin staining indicated that the cardiomyocyte cross sectional area in banded WTs was substantially increased, compared to banded inhibitor-1 hearts (n>120 myocytes from 3 mice per group) (FIG. 6A). Given the anti-hypertrophic effects of inhibitor-1, PKC, calcineurin, CREB and MAP-kinase hypertrophic pathways were examined. There was a significant decrease in p38 and ERK1/2 activation in the banded TGs compared to WT cohorts (FIG. 6B).

The protective effects of inhibitor-1 were not associated with any alterations in the levels of phospholamban, SERCA and calsequestrin but the phosphorylation of phospholamban at Ser16 was markedly increased (FIG. 6C). Of note, no differences were observed in phospholamban phosphorylation at Thr17 or in the Ser2809 phosphorylation of the ryanodine receptor. Accordingly, the example likewise shows that active inhibitor-1 expression protects mice subjected to aortic banding from cardiac hypertrophy at the cellular level, attenuates activation of MAP-kinase pathways and has beneficial effects on phospholamban phosphorylation.

Example 7

Active Inhibitor-1 Expression Rescues a Rat Model of Pressure-Overload Hypertrophy in Transition to Failure To investigate whether short-term expression of the active inhibitor-1 by adenoviral gene transfer could improve hemodynamic parameters in the setting of pre-existing heart failure, a rat model of pressure overload induced cardiomyopathy was utilized, which exhibits increased left ventricular-diastolic dimensions and decreased fractional shortening by 22 weeks post-banding (del Monte F., et al., *Circulation.* 2001; 104:1424-9) Four-week old Wistar rats (70-80 g) were obtained from Charles River Laboratories (Wilmington, Mass.) and aortic constriction was performed as previously described. (del Monte, F., et al., *Circulation.* 2001; 104:1424-9). The animals were initially randomized in two groups: one group of 30 animals with aortic banding and a second group of 32 animals, which were sham-operated. All animals survived the initial operation.

When decreases of more than 25% in left ventricular fractional shortening were observed, gene transfer was performed. The group of 30 animals with aortic banding was subdivided in two groups of fifteen with each group receiving either Ad.I-1T35D or Ad.GFP. The group of 24 sham-operated animals did not receive any gene transfer and were studied in an age-matched fashion. One animal in the I-1T35D group and one animal in the GFP group died during the gene transfer surgery. The adenoviral delivery system has been described previously (Beeri R., et al., *Circulation.* 2002; 106: 1756-9). In the sham-operated rats, no gene delivery was performed. Previous studies have shown that the sham-operated rats injected with Ad.GFP behaved in a similar way as non-infected sham operated rats. Adenoviral gene delivery of active inhibitor-1 or the reporter gene GFP with a catheter-based approach induced an expression pattern that was grossly homogenous throughout the ventricles in failing and non-failing hearts (Del Monte, F., et al., *Physiol Genomics.* 2002; 9:49-56).

Adenoviral vectors were generated (Del Monte, F., et al., *Circulation.* 1999; 100:2308-11) and delivered (Beeri R., et al. *Circulation.* 2002; 106:1756-9) in the rat heart failure model (Beeri R., et al. *Circulation.* 2002; 106:1756-9; Del Monte, et al., *Circulation.* 2001; 104:1424-9). Pressure measurements and biochemical assays (upon termination) were performed as previously described (Beeri R., et al. *Circulation.* 2002; 106:1756-9; Del Monte, et al., *Circulation.* 2001; 104:1424-9).

Figure 7:
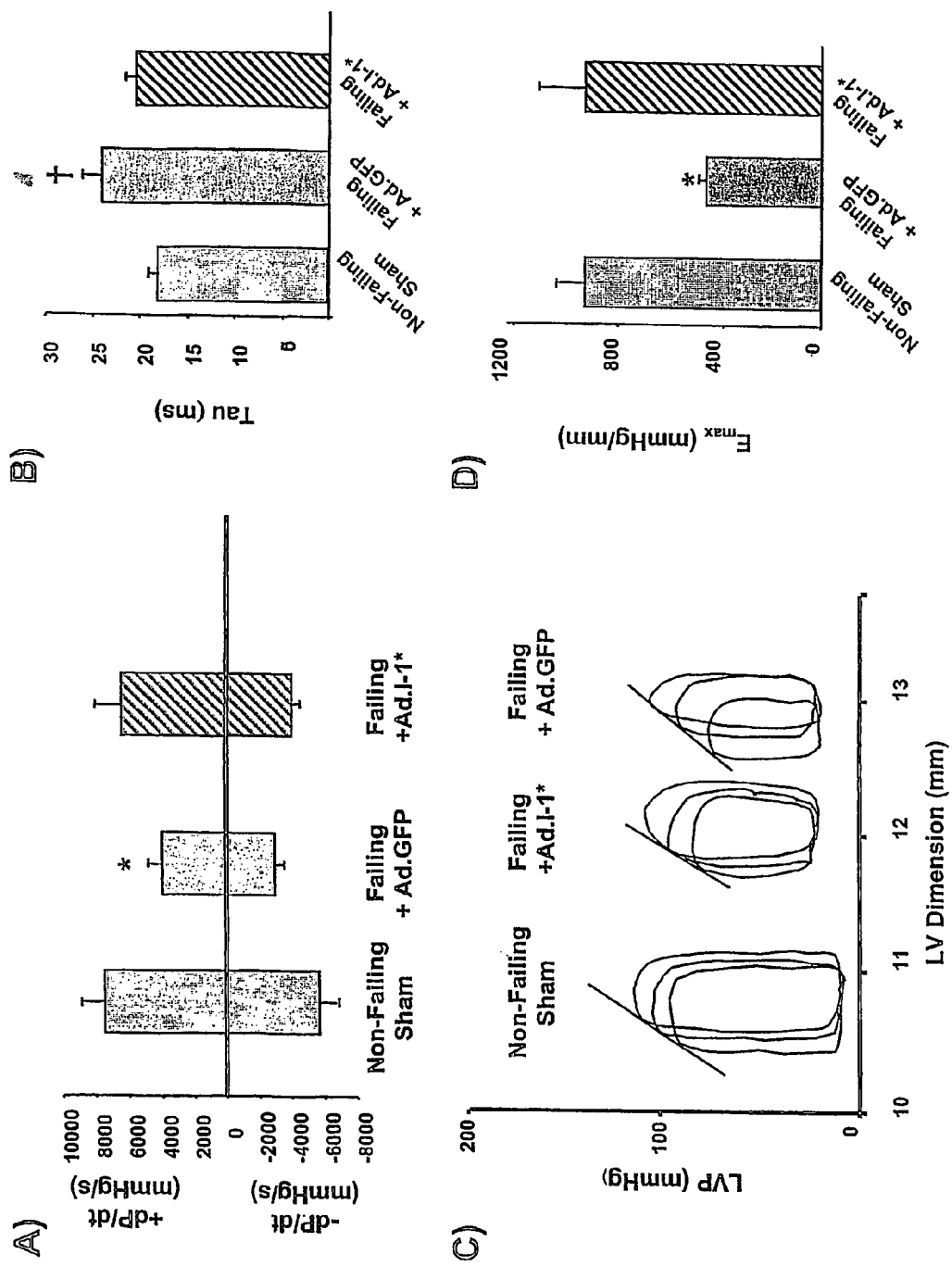
FIG. 7A shows, in bar-graph form, measurements of intraventricular pressure in the sham operated non-failing hearts, failing hearts infected with GFP (Ad.GFP), and failing hearts sham operated non-failing hearts, failing hearts infected with GFP (Ad.GFP), and failing hearts infected with the active inhibitor-1 (Ad.I-1*) groups. *P<0.05 versus the non-failing sham operated group, n=7-9 rats per group.
FIG. 7B shows, in bar-graph form, measurements of the isovolumic relaxation coefficient (tau). gP<0.10 versus the non-failing group, n=7-9 rats per group.
FIG. 7C shows the cardiac left ventricular pressure versus left ventricular dimension loops (P-V loops), as determined by piezoelectric crystals in non-failing hearts, failing+GFP hearts, and failing+active inhibitor-1 hearts. n=7-9 rats per group.
FIG. 7D shows, in bar-graph form, the maximal elastance ($E_{max}$), derived from the end-systolic pressure-dimension relationship. *P<0.05, n=7-9 rats per group.

Immunoblotting studies also confirmed the expression of active inhibitor-1 and protein phosphatase 1 activity was significantly reduced (60%) upon infection with Ad.I-1* (data not shown). The left ventricular function was decreased in the failing control group (FIG. 7A), but gene transfer of the active inhibitor-1 significantly increased the rate of pressure rise (+dP/dt) (FIG. 7A). Diastolic parameters were also normalized by active inhibitor-1 expression, as evidenced by restoration of the maximal rate of decline of left ventricular systolic pressure (−dP/dt), as well as the time course for pressure decline, measured by tau, the isovolumic relaxation constant (FIG. 7B).

To further define ventricular function in a load-independent fashion, pressure-dimension analysis was performed in a subset of animals (FIG. 7C). Pressure measurements were performed as previously described (Del Monte, F., et al., *Circulation.* 2001; 104:1424-9). The time course of isovolumic relaxation ($\tau$) was calculated using the equation: $P = P_o e^{-\tau} + P_B$, where P is the left ventricular isovolumic pressure, $P_o$ is pressure at the time of peak −dP/dt, and $P_B$ is residual pressure. For the pacing studies, an epicardial lead was placed at on atrial appendage connected to a stimulator (Grass Instruments, MA). In a subset of animals, multiple 0.7 mm piezoelectric crystals (Sonometrics Co., Canada) were placed over the surface of the left ventricle along the short axis of the ventricle at the level of the mitral valve to measure the inter-crystal distance. Left ventricular pressure-dimension loops were generated under different loading conditions by clamping the inferior vena cava. The end-systolic pressure-dimension relationship was obtained by producing a series of pressure dimension loops over a range of loading conditions and connecting the upper left hand corners of the individual pressure-dimension loops to generate the maximal slope.

To alter loading conditions, the inferior vena cava was clamped in the open-chested animals, thereby reducing ventricular volume. This allowed the calculation of the end-systolic pressure dimension relationship, using a series of measurements under varying pre-load conditions (FIG. 7C). The maximal slope of the end-systolic pressure dimension relationship ($E_{max}$, or Maximal Elastance) was lower in control failing hearts, infected with control virus (Ad.GFP), compared to non-failing, indicating a diminished state of intrinsic myocardial contractility and contractile reserve. Expression of the active inhibitor-1 completely restored the slope of the end-systolic pressure dimension relationship to non-failing levels (FIG. 7D), indicating that the heart's ability to enhance contractility in the face of increasing preload was restored. Thus, acute adenoviral expression of the active inhibitor-1 halts the progression of cardiac dysfunction and decompensation in a rat model of pressure overload induced heart failure, as per the above-delineated results.

Additional determination of phosphatase activities were also performed using (Schwinger, R. H., *Circulation.* 1995; 92:3220-8) P-labeled Myelin Basic Protein (NEB Catalog #P0780S), using okadaic acid to differentiate PP1 and PP2A activity, as described previously (Margolis, S. S., *Embo J.* 2003; 22:5734-45). Glycogen synthase (GS) and glycogen phosphorylase (GP) activities were determined in cardiac muscle homogenates (Suzuki, Y., et al., *Mol. Cell Biol.* 2001; 21:2683-94). GS activity was determined by the transfer of [$^{14}$C] glucose from UDP [$^{14}$C] glucose into glycogen, in the presence or absence of 7.2 mM glucose-6-phosphate, an allosteric effector of glycogen synthase activity. Glycogen phosphorylase activity was assayed by measuring incorporation of [$^{14}$C] glucose from [$^{14}$C] glucose-1-phosphate into glycogen in the absence or presence of 2 mM AMP, an allosteric activator of glycogen phosphorylase.

Figure 8:
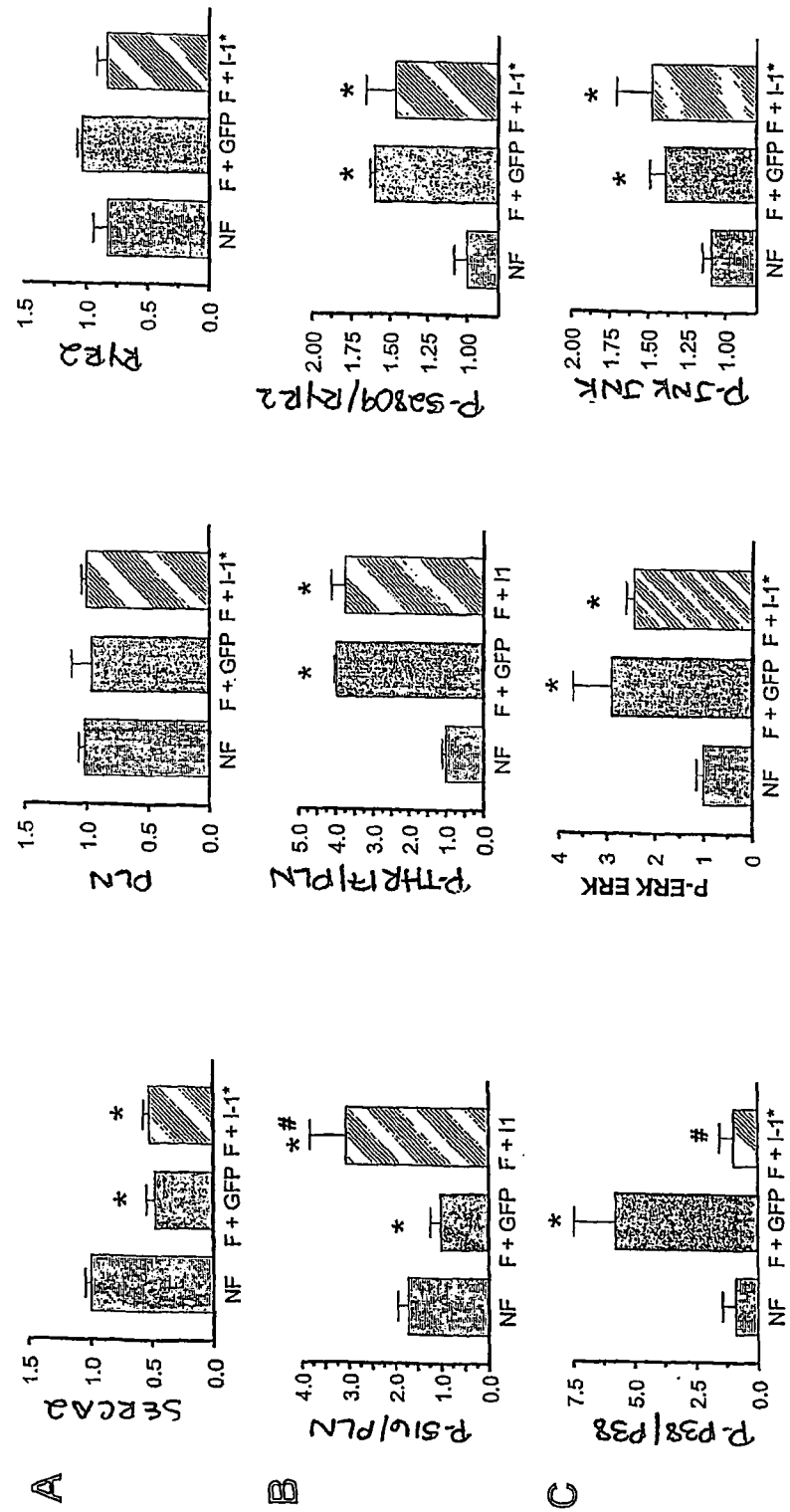
FIG. 8A shows, in bar-graph form, the results of quantitative immunoblotting for the levels of SERCA2, phospholamban (PLN), and the cardiac ryanodine receptor (RYR2) in the failing vs. non-failing heart groups.
FIG. 8B shows, in bar-graph form, the levels of phosphorylation of phospholamban at Ser16 and Thr17 and the ryanodine receptor at Ser2809 in the failing vs. non-failing heart groups.
FIG. 8C shows, in bar-graph form, the levels of MAP-kinase activation (p38, ERK and JNK) in the failing vs. non-failing heart groups. *P<0.05 versus NF and #P<0.05 vs. F+GFP, n=4 hearts per group.

The biochemical characterization revealed that the SERCA2a levels were significantly decreased in the failing hearts, consistent with previous reports (Del Monte, F., et al., *Circulation.* 2001; 104:1424-9), and these levels remained depressed upon control (Ad.GFP) or active inhibitor-1 gene transfer. The levels of phospholamban or the ryanodine receptor were not different (FIG. 8A). Phosphorylation of phospholamban at serine 16, the cAMP-dependent site, was significantly depressed in failing hearts, but adenoviral gene transfer of the active inhibitor-1 was associated with a substantial increase in phosphorylation of serine 16 (FIG. 8B). Interestingly, both failing groups infected with either control or active inhibitor-1 virus, exhibited increases in the Thr-17 phosphorylation in phospholamban (FIG. 8B).

Figure 10:
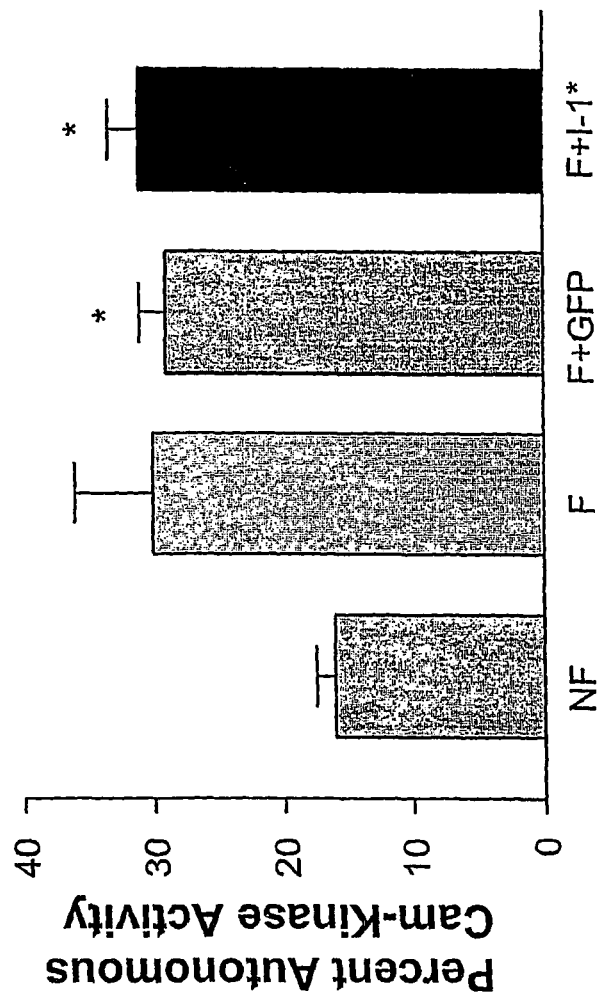
FIG. 10 shows, in bar-graph form, CaM-Kinase activity in the failing vs. non-failing heart groups.

Further examination revealed that the CAM-kinase activity was significantly increased in these hearts (FIG. 10 and Table 1, below).

TABLE 1

Echocardiographic Measures in Rats after Sham Surgery or Aortic Banding

|  | PW (mm) | LVDD (mm) | LVSD (mm) | FS (%) |
|---|---|---|---|---|
| Sham |  |  |  |  |
| 12 weeks | 1.9 ± 0.1 | 8.3 ± 0.3 | 4.9 ± 0.2 | 46 ± 5 |
| 24 weeks | 1.9 ± 0.1 | 8.7 ± 0.3 | 5.0 ± 0.2 | 43 ± 2 |
| Banded |  |  |  |  |
| 12 weeks | 2.7 ± 0.2* | 8.6 ± 0.2 | 4.3 ± 0.2 | 48 ± 5* |
| 20-24 weeks | 2.8 ± 0.20* | 10 ± 0.3* | 6.1 ± 0.1* | 31 ± 2*† |

PW: posterior wall thickness during diastole, LVDD: Left ventricular Diameter during diastole, LVSD: Left ventricular Systolic Diameter during Systole FS: Fractional shortening,
*p < 0.05 compared to sham at similar time period
†p < 0.05 compared to values at 12 weeks The activity of CaM-Kinase is increased in failing (F) rat hearts and in failing rat hearts infected with Ad.I-1* or Ad.GFP, compared to the non-failing (NF) control group. Interestingly, the phosphorylation level of serine 2809 in the ryanodine receptor was increased in all failing groups. Infection with the active inhibitor-1 had no effect on ryanodine receptor phosphorylation (FIG. 8B).

Examination of the effects of active inhibitor-1 gene transfer on MAP-kinase activation indicated a substantial decrease in activated p38-MAP-kinase with no alteration in the activation of ERK or JNK (FIG. 8C).

Example 8

Mechanism of Inhibitor-1 Effects in the Heart

Figure 9:
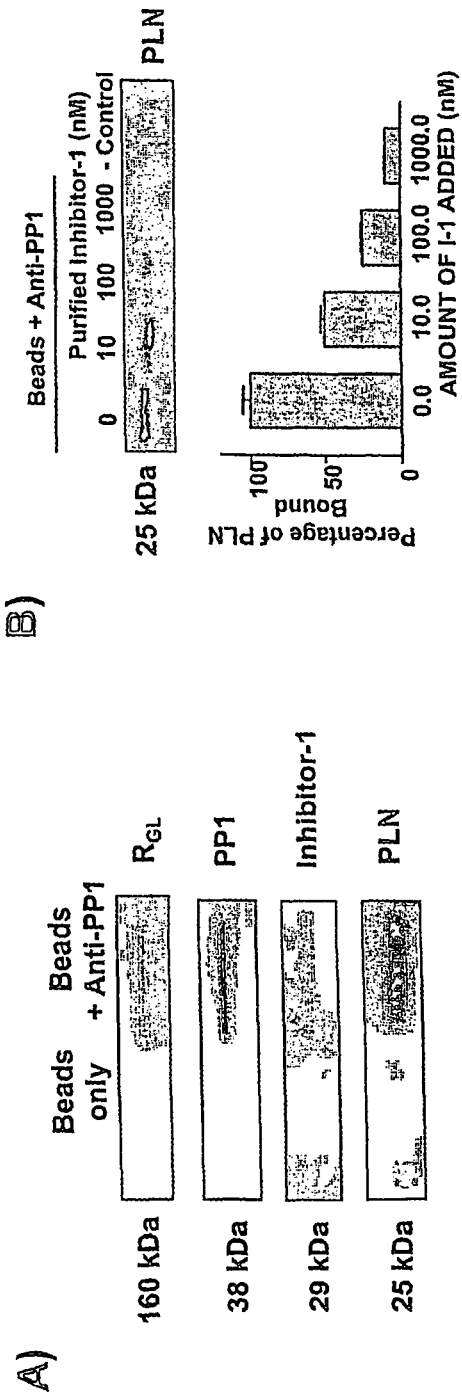
FIG. 9A shows a blot depicting the results of PP1 co-immunoprecipitation of inhibitor-1, phospholamban and $R_{GL}$.
FIG. 9B shows a blot depicting the results of adding exogenous, PKA-phosphorylated inhibitor-1 (10 nM to 1000 nM) to PP1 immunoprecipitated complexes, as measured in terms of dissociation of phospholamban from protein phosphatase 1 (n=3).

The findings above indicated that inhibitor-1 expression is associated with increased phospholamban phosphorylation. Accordingly, inhibitor-1 can selectively affect protein phosphatase 1 substrates in vivo. To further substantiate this observation, immunoprecipitation experiments were performed with an antibody to the protein phosphatase 1 (a-isoform) catalytic subunit. For the inhibitor-1 competition binding assays, immunoprecipitations were performed as described earlier. After the removal of the unbound cardiac homogenates, the beads were washed (5×, PBS plus 0.1% Tween20) and then incubated with 500 µl of purified and phosphorylated inhibitor-1 at varying final concentrations (10 nM to 1000 nM). The beads were then washed (3×) and bound proteins were eluted with 0.1 M citric acid (pH 2.8). Of note, inhibitor-1, the SR/glycogen targeting subunit of protein phosphatase 1 ($R_{GL}$) (Tang, P. M., et al., *J. Biol Chem* 1991; 266:15782-9) and phospholamban were co-immunoprecipitated with protein phosphatase 1 (FIG. 9A). Incubation of this complex with increasing concentrations (10 nM to 1000 nM) of purified and phosphorylated inhibitor-1 revealed reduced binding of phospholamban, in a dose dependent manner (FIG. 9B).

Other embodiments are within the following claims.

What is claimed is:

1. A method of increasing cardiac contractility and reducing morphological deterioration associated with cardiac remodeling in a subject with existing heart failure, said method comprising:
    directly introducing in vivo an effective amount of a viral vector into the lumen of a coronary artery of the heart of the subject by percutaneous intracoronary gene transfer, wherein said viral vector is an adeno-associated viral vector (AAV) comprising a nucleic acid sequence encoding a polypeptide consisting of amino acids 1-65 of SEQ ID NO: 2, wherein threonine at position 35 of SEQ ID NO: 2 is replaced with an aspartic acid; and wherein said nucleic acid sequence is operably linked to a promoter capable of directing expression in the heart;
    thereby expressing the fragment in the heart of the subject in an amount effective to increase cardiac contractility and reduce morphological deterioration associated with cardiac remodeling in the subject with existing heart failure.

2. The method of claim 1, wherein the promoter is a tissue specific promoter, a smooth muscle specific promoter, a cardiac specific promoter, or a viral promoter.

3. The method of claim 1, wherein the promoter is a constitutive promoter.

4. The method of claim 2, wherein the tissue specific promoter is a cardiac troponin T promoter, myosin heavy chain or the myosin light chain promoter, cardiac myosin promoter, troponin T promoter, BNP promoter, alpha actin promoter, or a SM22a promoter.

5. The method of claim 1, wherein the viral vector is selected from the group consisting of an adeno-associated virus-1 (AAV1), AAV2, AAV3, AAV4, AAV5, AAV6, AAV7, AAV8 and AAV9.

6. The method of claim 1, wherein the increase in contractility is determined by increased myocyte shortening (myocyte length change), rates of myocyte cell shortening (dL/dt) and relengthening (−dL/dt), a lower time constant for relaxation (tau($\tau$)), and accelerated calcium signal decay.

7. The method of claim 1, wherein the protection against morphological deterioration associated with cardiac remodeling is determined by measuring the heart-to-body weight ratio, infarct size, and the presence of cardiac fibrosis, wherein protection is present if expression of said human phosphatase inhibitor-1 results in a reduced heart-to-body weight ratio, a decreased infarct size, or reduced cardiac fibrosis as compared to a control.

8. The method of claim 1, wherein the heart failure comprises ischemia, arrhythmia, myocardial infarction, abnormal heart contractility, or abnormal $Ca^{2+}$ metabolism.

9. The method of claim 1, wherein the coronary artery is the left anterior descending artery (LAD) or the distal circumflex artery (LCX).

10. The method of claim 1, wherein the method further comprises restricting blood flow to one or more of the great coronary vein (GCV), the middle cardiac vein (MCV), or the anterior interventricular vein (AIV).

11. The method of claim 9, wherein the vector is introduced into the lumen of the coronary artery after ischemic preconditioning of the left anterior descending artery (LAD) and/or the distal circumflex artery (LCX).

12. The method of claim 1, wherein the vector is introduced into the lumen of the coronary artery with a catheter.

13. The method of claim 9, wherein the coronary artery is the distal circumflex artery (LCX).

14. The method of claim 9, wherein the coronary vessel is the left anterior descending artery (LAD).

15. The method of claim 1, wherein the amount of the viral vector is between $1\times10^{11}$ and $1\times10^{16}$ plaque forming units.

16. The method of claim 1, wherein the viral vector is adeno-associated virus serotype 9 (AAV9).

* * * * *